(12) United States Patent
Kehler et al.

(10) Patent No.: US 10,005,764 B2
(45) Date of Patent: Jun. 26, 2018

(54) HALOGENATED QUINAZOLIN-THF-AMINES AS PDE1 INHIBITORS

(71) Applicant: H. Lundbeck A/S, Valby (DK)

(72) Inventors: Jan Kehler, Lyngby (DK); Lars Kyhn Rasmussen, Vanløse (DK); Morten Langgård, Glostrup (DK)

(73) Assignee: H. Lundbeck A/S, Valby (DK)

( * ) Notice: Subject to any disclaimer, the term of this patent is extended or adjusted under 35 U.S.C. 154(b) by 0 days. days.

(21) Appl. No.: 15/301,210

(22) PCT Filed: Mar. 27, 2015

(86) PCT No.: PCT/EP2015/056713
§ 371 (c)(1),
(2) Date: Sep. 30, 2016

(87) PCT Pub. No.: WO2015/150254
PCT Pub. Date: Oct. 8, 2015

(65) Prior Publication Data
US 2017/0022186 A1    Jan. 26, 2017

(30) Foreign Application Priority Data

Apr. 4, 2014  (DK) .................................. 2014 00194

(51) Int. Cl.
*C07D 405/12* (2006.01)
*C07D 403/12* (2006.01)
*C07D 491/048* (2006.01)

(52) U.S. Cl.
CPC ......... *C07D 405/12* (2013.01); *C07D 403/12* (2013.01); *C07D 491/048* (2013.01)

(58) Field of Classification Search
CPC .................................................. C07D 405/12
See application file for complete search history.

(56) References Cited

FOREIGN PATENT DOCUMENTS

| WO | WO 2007/096743 | 8/2007 |
|---|---|---|
| WO | WO 2007/103370 | 9/2007 |
| WO | WO 2015/150438 A1 | 10/2015 |
| WO | WO 2015/150440 A1 | 10/2015 |
| WO | WO 2015/150564 A1 | 10/2015 |
| WO | WO 2015/150565 A1 | 10/2015 |
| WO | WO 2015/150995 A1 | 10/2015 |

OTHER PUBLICATIONS

International Search Report PCT/EP2015/056713 (WO 2015/150254) (2015) (3 pages).
Written Opinion of the International Searching Authority PCT/EP2015/056713 (WO 2015/150254) (2015) (5 pages).

*Primary Examiner* — Paul V Ward
(74) *Attorney, Agent, or Firm* — Wolf, Greenfield & Sacks, P.C.

(57) ABSTRACT

The present invention provides halogenated quinazolin-THF-amines as PDE1 inhibitors and their use as a medicament, in particular for the treatment of neurodegenerative disorders and psychiatric disorders.

15 Claims, No Drawings

HALOGENATED QUINAZOLIN-THF-AMINES AS PDE1 INHIBITORS

CROSS-REFERENCE TO RELATED APPLICATIONS

This Application is a § 371 Application of US Patent Application Serial No. PCT/EP2015/056713 (filed on Mar. 27, 2015; pending), which claims priority to Danish Patent Application PA 2014 00194 (filed on Apr. 4, 2014).

FIELD OF THE INVENTION

The present invention provides compounds that are PDE1 enzyme inhibitors and their use as a medicament, in particular for the treatment of neurodegenerative disorders and psychiatric disorders. The present invention also provides pharmaceutical compositions comprising compounds of the invention and methods of treating disorders using the compounds of the invention.

BACKGROUND OF THE INVENTION

Throughout this application, various publications are referenced in full. The disclosures of these publications are hereby incorporated by reference into this application to describe more fully the state of the art to which this invention pertains.

The second messenger cyclic Nucleotides (cNs), cyclic adenosine monophosphate (cAMP) and cyclic guanosine monophosphate (cGMP) play a major role in intracellular signal transduction cascade, by regulating cN-dependent protein kinases (PKA and PKG), EPACs (Exchange Protein Activated by cAMP), phosphoprotein phosphatases, and/or cN-gated cation channels. In neurons, this includes the activation of cAMP- and cGMP-dependent kinases and subsequent phosphorylation of proteins involved in acute regulation of synaptic transmission as well as in neuronal differentiation and survival. Intracellular concentrations of cAMP and cGMP are strictly regulated by the rate of biosynthesis by cyclases and by the rate of degradation by phosphodiesterases (PDEs, EC 3.1.4.17). PDEs are bimetallic hydrolases that inactivate cAMP/cGMP by catalytic hydrolysis of the 3'-ester bond, forming the inactive 5'-monophosphate. Since PDEs provide the only means of degrading the cyclic nucleotides cAMP and cGMP in cells, PDEs play an essential role in cyclic nucleotide signalling. The catalytic activities of PDEs provide for breakdown of cNs over a spectrum of concentrations in all cells, and their varied regulatory mechanisms provide for integration and crosstalk with myriad signalling pathways. Particular PDEs are targeted to discrete compartments within cells where they control cN level and sculpt microenvironments for a variety of cN signalosomes (Sharron H. Francis, Mitsi A. Blount, and Jackie D. Corbin. Physiol Rev 2011, 91: 651-690).

On the basis of substrate specificity, the PDE families can be divided into three groups: 1) The cAMP-specific PDEs, which include PDE4, PDE7, and PDE8, 2) the cGMP-selective enzymes PDE5 and PDE9, and 3) the dual-substrate PDEs, PDE1, PDE2, PDE3, as well as PDE10 and PDE11.

Previously named calmodulin-stimulated PDE (CaM-PDE), PDE1 is unique in that it is $Ca^{2+}$-dependently regulated via calmodulin (CaM, a 16 kDa $Ca^{2+}$-binding protein) complexed with four $Ca^{2+}$ (for review, Sharron H. Francis, Mitsi A. Blount, and Jackie D. Corbin. Physiol Rev 2011, 91: 651-690). Thus, this family represents an interesting regulatory link between cyclic nucleotides and intracellular $Ca^{2+}$. The PDE1 family is encoded by three genes: PDE1A (mapped on human chromosome 2q32), PDE1B (human chromosome location, hcl: 12q13) and PDE1C (hcl: 7p14.3). They have alternative promoters and give rise to a multitude of proteins by alternative splicing which differ in their regulatory properties, substrate affinities, specific activities, activation constants for CaM, tissue distribution and molecular weights. More than 10 human isoforms are identified. Their molecular weights vary from 58 to 86 kDa per monomer. The N-terminal regulatory domain that contains two $Ca^{2+}$/CaM binding domains and two phosphorylation sites differentiate their corresponding proteins and modulate their biochemical functions. PDE1 is a dual substrate PDE and the PDE1C-subtype has equal activity towards cAMP and cGMP (Km≈1-3 µM), whereas the subtypes PDE1A and PDE1B has a preference for cGMP (Km for cGMP≈1-3 µM and for cAMP≈10-30 µM).

The PDE1 subtypes are highly enriched in the brain and located especially in the striatum (PDE1B), hippocampus (PDE1A) and cortex (PDE1A) and this localization is conserved across species (Amy Bernard et al. Neuron 2012, 73, 1083-1099). In the cortex, PDE1A is present mainly in deep cortical layers 5 and 6 (output layers), and used as a specificity marker for the deep cortical layers. PDE1 inhibitors enhance the levels of the second messenger cNs leading to enhanced neuronal excitability.

Thus, PDE1 is a therapeutic target for regulation of intracellular signalling pathways, preferably in the nervous system and PDE1 inhibitors can enhance the levels of the second messengers cAMP/cGMP leading to modulation of neuronal processes and to the expression of neuronal plasticity-related genes, neurotrophic factors, and neuroprotective molecules. These neuronal plasticity enhancement properties together with the modulation of synaptic transmission make PDE1 inhibitors good candidates as therapeutic agents in many neurological and psychiatric conditions. The evaluation of PDE1 inhibitors in animal models (for reviews see e.g. Blokland et al. Expert Opinion on Therapeutic Patents (2012), 22(4), 349-354; and Medina, A. E. Frontiers in Neuropharmacology (2011), 5(February), 21) have suggested the potential for the therapeutic use of PDE1 inhibitors in neurological disorders, like e.g. Alzheimer's, Parkinson's and Huntington's Diseases and in psychiatric disorders like e.g. Attention Deficit Hyperactivity Disorder (ADHD), restless leg syndrome, depression, narcolepsy, cognitive impairment and cognitive impairment associated with schizophrenia (CIAS). There have also been patent applications claiming that PDE1 inhibitors are useful in diseases that may be alleviated by the enhancement of progesterone-signalling such as female sexual dysfunction e.g. WO-2010065153.

SUMMARY OF THE INVENTION

PDE1 enzymes are expressed in the Central Nervous System (CNS), making this gene family an attractive source of new targets for the treatment of psychiatric and neurodegenerative disorders.

The compounds of the invention may offer alternatives to current marketed treatments for neurodegenerative and/or psychiatric disorders, which are not efficacious in all patients. Hence, there remains a need for alternative methods of treatment.

The objective of the present invention is to provide compounds that are PDE1 inhibitors, and as such are useful to treat neurodegenerative disorders and psychiatric disorders. In a preferred embodiment the compounds are selective PDE1 inhibitors.

Accordingly, the present invention relates to compounds of formula (I)

(I)

wherein

X is halogen, preferably fluorine or chlorine or bromine;

$R_1$ is selected from the group consisting of H and $C_1$-$C_3$ alkyl, wherein the alkyl optionally may be substituted one, two or three times with fluorine;

$R_2$ is selected from the group consisting of H and $C_1$-$C_4$ alkyl, wherein the $C_1$-$C_4$ alkyl optionally is substituted one or more times with one or more substituents, $R_3$ is selected from the group consisting of H and $C_1$-$C_6$ alkyl, wherein the $C_1$-$C_6$ alkyl optionally is substituted one or more times with one or more substituents, $R_4$ and $R_5$ independently of each other are selected from the group consisting of H, $C_1$-$C_6$ alkyl, optionally is substituted one or more times with one or more substituents, $C_3$-$C_6$ cycloalkyl, fluorine, chlorine, hydroxy and alkoxy, $R_6$ and $R_7$ independently of each other are selected from the group consisting of H and $C_1$-$C_6$ alkyl, wherein the $C_1$-$C_6$ alkyl optionally is substituted one or more times with one or more substituents, $R_8$ and $R_9$ independently of each other are selected from the group consisting of H and $C_1$-$C_6$ alkyl, wherein the $C_1$-$C_6$ alkyl optionally is substituted one or more times with one or more substituents, and pharmaceutically acceptable acid addition salts of Compound I, racemic mixtures of Compound I, or the corresponding enantiomer and/or diastereo-isomer of Compound I, and polymorphic forms of Compound I as well as tautomeric forms of Compound I.

DETAILED DESCRIPTION OF THE INVENTION

Embodiments of the Invention

In a first embodiment (E1) the present invention relates to compounds of formula (I) (Compound I)

Compound (I)

wherein $R_1$ is selected from the group consisting of H and $C_1$-$C_3$ alkyl, wherein the alkyl optionally may be substituted one, two or three times with fluorine;

$R_2$ is selected from the group consisting of H and $C_1$-$C_4$ alkyl
  wherein $R_2$, when $R_2$ is a $C_1$-$C_4$ alkyl, may form a saturated five membered aliphatic ring with $R_9$
  wherein the $C_1$-$C_4$ alkyl optionally is substituted one or more times with one or more substituents independently selected from the group consisting of phenyl, monocyclic 5- or 6-membered heteroaryl, $C_3$-$C_6$ cycloalkyl, fluorine, chlorine, and alkoxy of the form —$OR_{10}$
    wherein $R_{10}$ is $C_1$-$C_5$ alkyl;

$R_3$ is selected from the group consisting of H and $C_1$-$C_6$ alkyl
  wherein the $C_1$-$C_6$ alkyl optionally is substituted one or more times with one or more substituents independently selected from the group consisting of phenyl, monocyclic 5- or 6-membered heteroaryl, $C_3$-$C_6$ cycloalkyl, fluorine, chlorine, and alkoxy of the form —$OR_{10}$
    wherein $R_{10}$ is $C_1$-$C_5$ alkyl;

$R_4$ and $R_5$ independently of each other are selected from the group consisting of H, $C_1$-$C_6$ alkyl, $C_3$-$C_6$ cycloalkyl, fluorine, chlorine, hydroxy and alkoxy of the form —$OR_{10}$
  wherein the $C_1$-$C_6$ alkyl optionally is substituted one or more times with one or more substituents independently selected from the group consisting of phenyl, monocyclic 5- or 6-membered heteroaryl, $C_3$-$C_6$ cycloalkyl, fluorine, chlorine, and alkoxy of the form —$OR_{10}$
    wherein $R_{10}$ is $C_1$-$C_5$ alkyl;

$R_6$ and $R_7$ independently of each other are selected from the group consisting of H and $C_1$-$C_6$ alkyl
  wherein the $C_1$-$C_6$ alkyl optionally is substituted one or more times with one or more substituents independently selected from the group consisting of $C_3$-$C_6$ cycloalkyl, fluorine, chlorine, and alkoxy of the form —$OR_{10}$
    wherein $R_{10}$ is $C_1$-$C_5$ alkyl;

$R_8$ and $R_9$ independently of each other are selected from the group consisting of H and $C_1$-$C_6$ alkyl
  wherein $R_9$, when $R_9$ is a $C_1$-$C_6$ alkyl, may form a saturated aliphatic five membered ring with $R_2$
  wherein the $C_1$-$C_6$ alkyl optionally is substituted one or more times with one or more substituents independently selected from the group consisting of $C_3$-$C_6$ cycloalkyl, fluorine, chlorine, and alkoxy of the form —$OR_{10}$ wherein $R_{10}$ is $C_1$-$C_5$ alkyl;

and/or pharmaceutically acceptable acid addition salts of Compound I, racemic mixtures of Compound I, or the corresponding enantiomer and/or optical isomer of Compound I, and polymorphic forms of Compound I as well as tautomeric forms of Compound I.

In an embodiment (E2) of (E1) $R_2$ is H or —$CH_3$.

In an embodiment (E3) of any of (E1) and (E2) at least one of $R_6$ and $R_7$ is H.

In an embodiment (E4) of (E3) both $R_6$ and $R_7$ are H.

In an embodiment (E5) of (E1) at least four of $R_3$ to $R_9$ are H.

In an embodiment (E6) of (E1) when any of $R_3$, $R_4$ or $R_5$ are alkyl, then at most one of them is substituted at most once with phenyl or monocyclic 5- or 6-membered heteroaryl.

In an embodiment (E7) of (E1) $R_2$ and $R_9$ form a five-membered saturated aliphatic ringsystem.

In an embodiment (E8) of (E1) $R_1$ is substituted one time with fluorine.

In an embodiment (E9) of (E1) $R_1$ is substituted two times with fluorine.

In an embodiment (E10) of (E1) $R_1$ is substituted three times with fluorine.

In an embodiment (E11) of (E1) X is fluorine.

In an embodiment (E12) of (E1) X is chlorine.

In an embodiment (E13) of any of (E1) to (E12) the compound is selected from the group of compounds listed in Table 1.

In an embodiment (E14) of any of (E1) to (E13) the compound is a PDE1A inhibitor.

In an embodiment (E15) of any of (E1) to (E13) the compound is a PDE1B inhibitor.

In an embodiment (E16) of any of (E1) to (E13) the compound is a PDE1C inhibitor.

In an embodiment (E17) the compound of any of (E1) to (E16) is for use as a medicament.

In an embodiment (E18) the compound of any of (E1) to (E16) is use in the treatment of attention-deficit/hyperactivity disorder (ADHD)

Embodiment (E19): A pharmaceutical composition comprising the compound of any of (E1) to (E16) and one or more pharmaceutically acceptable carriers.

Embodiment (E20): A pharmaceutical composition according to (E19) for use in a method of treatment of attention-deficit/hyperactivity disorder (ADHD)

Embodiment (E21): A compound of any one of (E1) to (E16) for use in a method for the treatment of attention-deficit/hyperactivity disorder (ADHD)

Embodiment (E22): A compound of any one of (E1) to (E16) for the preparation of a medicament for use in the treatment of attention-deficit/hyperactivity disorder (ADHD).

Embodiment (E23): A method of treating a subject suffering of attention-deficit/hyperactivity disorder (ADHD) which method comprises administering an effective amount of a compound of any one (E1) to (E16).

Embodiment (E24): A pharmaceutical composition according to (E19) for use in a method of treatment of neurodegenerative disorder.

Embodiment (E25): A compound of any one of (E1) to (E16) for use in a method for the treatment of neurodegenerative disorder.

Embodiment (E26): A compound of any one of (E1) to (E16) for the preparation of a medicament for use in the treatment of neurodegenerative disorder.

Embodiment (E27): A method of treating a subject suffering of a neurodegenerative disorder which method comprises administering an effective amount of a compound of any one (E1) to (E16).

In an embodiment (E28) of any of embodiments (E24) to (E27) the neurodegenerative disorder is selected from the group consisting of Alzheimer's Disease, Parkinson's Disease and Huntington's Disease or for the treatment of a psychiatric disorder such as Attention Deficit hyperactivity Disorder (ADHD), depression, narcolepsy, cognitive impairment and cognitive impairment associated with schizophrenia (CIAS).

Embodiment (E29): Use of a compound of any of claims 1-7 in the manufacture of a medicament for the treatment of a neurodegenerative disorder, such as Alzheimer's Disease, Parkinson's Disease and Huntington's Disease or for the treatment of a psychiatric disorder such as Attention Deficit hyperactivity Disorder (ADHD), depression, narcolepsy, cognitive impairment and cognitive impairment associated with schizophrenia (CIAS) or a brain disease like restless leg syndrome.

Embodiment (E30): In an embodiment (E30) of (E1) $R_1$ is H.

DEFINITIONS

PDE1 Enzymes

The PDE1 isozyme family includes numerous splice variant PDE1 isoforms. It has three subtypes, PDE1A, PDE1B and PDE1C which divide further into various isoforms. In the context of the present invention PDE1 and PDE1 enzymes are synonymous and refer to PDE1A, PDE1B and PDE1C enzymes as well as their isoforms.

Substituents

As used in the context of the present invention, the terms "halo" and "halogen" are used interchangeably and refer to fluorine, chlorine, bromine or iodine.

The terms "$C_1$-$C_3$ alkyl", "$C_1$-$C_4$ alkyl", "$C_1$-$C_5$ alkyl" and "$C_1$-$C_6$ alkyl" refer to a straight-chain or branched saturated hydrocarbon having from one to six carbon atoms, inclusive. Examples of such groups include, but are not limited to, methyl, ethyl, 1-propyl, 2-propyl, 1-butyl, 2-butyl, 2-methyl-2-propyl, 2-methyl-1-butyl, and n-hexyl.

The term "$C_3$-$C_6$ cycloalkyl" refers to cyclopropyl, cyclobutyl, cyclopentyl and cyclohexyl.

The expression "alkoxy" refers to a straight-chain or branched saturated alkoxy group having from one to six carbon atoms, inclusive, with the open valency on the oxygen. Examples of such groups include, but are not limited to, methoxy, ethoxy, n-butoxy, 2-methyl-pentoxy and n-hexyloxy.

The term "aryl" refers to a phenyl ring, optionally substituted with halogen, $C_1$-$C_6$ alkyl, $C_1$-$C_6$ alkoxy or halo($C_1$-$C_6$)alkyl as defined above.

The term "heteroaryl" refers to monocyclic- or polycyclic aromatic ring comprising carbon atoms, hydrogen atoms, and one or more heteroatoms, preferably, 1 to 3 heteroatoms, independently selected from nitrogen, oxygen, and sulfur. Illustrative examples of heteroaryl groups include, but are not limited to, pyridinyl, pyridazinyl, triazinyl, pyrrolyl, pyrazolyl, imidazolyl, (1,2,3,)- and (1,2,4)-triazolyl, pyrazinyl, pyrimidinyl, tetrazolyl, furanyl, thiophenyl, isoxazolyl, thiazolyl, isoxazolyl, and oxazolyl. A heteroaryl group can be unsubstituted or substituted with one or two suitable substituents. Preferably, the heteroaryl of this invention is a monocyclic 5 or 6 membered heteroaryl, wherein the ring comprises 2 to 5 carbon atoms and 1 to 3 heteroatoms, referred to herein as "monocyclic 5 or 6 membered heteroaryl".

Isomeric Forms

Where compounds of the present invention contain one or more chiral centers reference to any of the compounds will, unless otherwise specified, cover any of the enantiomerically or diastereomerically pure compounds as well as mixtures of the enantiomers or diastereomers in any ratio.

For example reference to the compound 8-fluoro-7-methoxy-N-(3-methyltetrahydrofuran-3-yl)quinazolin-4-amine without any further specification covers (R)-8-fluoro-7-methoxy-N-(3-methyltetrahydrofuran-3-yl)quinazolin-4-amine, (S)-8-fluoro-7-methoxy-N-(3-methyltetrahydrofuran-3-yl)quinazolin-4-amine as well as mixtures of the enantiomers in any ratio, including the racemic mixture (±)8-fluoro-7-methoxy-N-(3-methyltetrahydrofuran-3-yl)quinazolin-4-amine.

Correspondingly, reference to the compound 8-fluoro-7-methoxy-N-(2-methyltetrahydrofuran-3-yl)quinazolin-4-amine without any further specification covers all four stereoisomeric variants as well as mixtures thereof in any ratio, including the racemic mixtures.

The above also applies where compounds of the invention contain more than two chiral centers.

PDE1 Inhibitors

In the context of the present invention a compound is considered to be a PDE1 inhibitor if the amount required to reach the $IC_{50}$ level of PDE1B is 5 micro molar or less, preferably less than 4 micro molar, such as 3 micro molar or less, more preferably 2 micro molar or less, such as 1 micro molar or less, in particular 500 nM or less. In preferred embodiments the required amount of PDE1 inhibitor required to to reach the $IC_{50}$ level of PDE1B is 400 nM or less, such as 300 nM or less, 200 nM or less, 100 nM or less, or even 80 nM or less, such as 50 nM or less, for example 25 nM or less.

Pharmaceutically Acceptable Salts

The present invention also comprises pharmaceutically acceptable salts of the compounds. Such salts include acid addition salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutically acceptable inorganic or organic acid addition salts include the pharmaceutically acceptable salts listed in Berge, S. M. et al., J. Pharm. Sci. 1977, 66, 2, the contents of which are hereby incorporated by reference.

Furthermore, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Therapeutically Effective Amount

In the present context, the term "therapeutically effective amount" of a compound means an amount sufficient to cure, alleviate or partially arrest the clinical manifestations of a given disease and/or its complications in a therapeutic intervention comprising the administration of said compound. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

In the present context, the term "treatment" and "treating" means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to relief the symptoms and complications, and/or to prevent the condition, wherein prevention is to be understood as the management and care of a patient for the purpose of combating the disease, condition, or disorder and includes the administration of the active compounds to prevent the onset of the symptoms or complications. Nonetheless, prophylactic (preventive) and therapeutic (curative) treatments are two separate aspects of the invention. The patient to be treated is preferably a mammal, in particular a human being.

Pharmaceutical Compositions

The present invention further provides a pharmaceutical composition comprising a therapeutically effective amount of a compound of formula (I) and a pharmaceutically acceptable carrier or diluent. The present invention also provides a pharmaceutical composition comprising a therapeutically effective amount of one of the specific compounds disclosed in the Experimental Section herein and a pharmaceutically acceptable carrier or diluent.

The compounds of the invention may be administered alone or in combination with pharmaceutically acceptable carriers, diluents or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 21$^{th}$ Edition, Gennaro, Ed., Mack Publishing Co., Easton, Pa., 2005.

The pharmaceutical compositions may be specifically formulated for administration by any suitable route such as oral, rectal, nasal, pulmonary, topical (including buccal and sublingual), transdermal, intracisternal, intraperitoneal, vaginal and parenteral (including subcutaneous, intramuscular, intrathecal, intravenous and intradermal) routes. It will be appreciated that the route will depend on the general condition and age of the subject to be treated, the nature of the condition to be treated and the active ingredient.

Pharmaceutical compositions for oral administration include solid dosage forms such as capsules, tablets, dragees, pills, lozenges, powders and granules. Where appropriate, the compositions may be prepared with coatings such as enteric coatings or they may be formulated so as to provide controlled release of the active ingredient such as sustained or prolonged release according to methods well known in the art. Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Other suitable administration forms include, but are not limited to, suppositories, sprays, ointments, creams, gels, inhalants, dermal patches and implants.

Typical oral dosages range from about 0.001 to about 100 mg/kg body weight per day. Typical oral dosages also range from about 0.01 to about 50 mg/kg body weight per day. Typical oral dosages further range from about 0.05 to about 10 mg/kg body weight per day. Oral dosages are usually administered in one or more dosages, typically, one to three dosages per day. The exact dosage will depend upon the frequency and mode of administration, the sex, age, weight and general condition of the subject treated, the nature and severity of the condition treated and any concomitant diseases to be treated and other factors evident to those skilled in the art.

The formulations may also be presented in a unit dosage form by methods known to those skilled in the art. For illustrative purposes, a typical unit dosage form for oral administration may contain from about 0.01 to about 1000 mg, from about 0.05 to about 500 mg, or from about 0.5 mg to about 200 mg.

For parenteral routes such as intravenous, intrathecal, intramuscular and similar administration, typical doses are in the order of half the dose employed for oral administration.

The present invention also provides a process for making a pharmaceutical composition comprising mixing a therapeutically effective amount of a compound of formula (I) and at least one pharmaceutically acceptable carrier or diluent. In an embodiment, of the present invention, the compound utilized in the aforementioned process is one of the specific compounds disclosed in the Experimental Section herein.

The compounds of this invention are generally utilized as the free substance or as a pharmaceutically acceptable salt thereof. One example is an acid addition salt of a compound having the utility of a free base. When a compound of formula (I) contains a free base such salts are prepared in a conventional manner by treating a solution or suspension of a free base of formula (I) with a molar equivalent of a pharmaceutically acceptable acid. Representative examples of suitable organic and inorganic acids are described above.

For parenteral administration, solutions of the compounds of formula (I) in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The compounds of formula (I) may be readily incorporated into known sterile aqueous media using standard techniques known to those skilled in the art.

Suitable pharmaceutical carriers include inert solid diluents or fillers, sterile aqueous solutions and various organic solvents. Examples of solid carriers include lactose, terra alba, sucrose, cyclodextrin, talc, gelatin, agar, pectin, acacia, magnesium stearate, stearic acid and lower alkyl ethers of cellulose. Examples of liquid carriers include, but are not limited to, syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the compounds of formula (I) and a pharmaceutically acceptable carrier are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and optionally a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tabletted, placed in a hard gelatin capsule in powder or pellet form or it may be in the form of a troche or lozenge. The amount of solid carrier will vary widely but will range from about 25 mg to about 1 g per dosage unit. If a liquid carrier is used, the preparation may be in the form of a syrup, emulsion, soft gelatin capsule or sterile injectable liquid such as an aqueous or non-aqueous liquid suspension or solution.

The pharmaceutical compositions of the invention may be prepared by conventional methods in the art. For example, tablets may be prepared by mixing the active ingredient with ordinary adjuvants and/or diluents and subsequently compressing the mixture in a conventional tableting machine prepare tablets. Examples of adjuvants or diluents comprise: corn starch, potato starch, talcum, magnesium stearate, gelatin, lactose, gums, and the like. Any other adjuvants or additives usually used for such purposes such as colorings, flavorings, preservatives etc. may be used provided that they are compatible with the active ingredients.

Treatment of Disorders

As mentioned above, the compounds of formula (I) are PDE1 enzyme inhibitors and as such are useful to treat associated neurological and psychiatric disorders.

The invention thus provides a compound of formula (I) or a pharmaceutically acceptable acid addition salt thereof, as well as a pharmaceutical composition containing such a compound, for use in the treatment of a neurodegenerative disorder, psychiatric disorder or drug addiction in mammals including humans; wherein the neurodegenerative disorder is selected from the group consisting of Alzheimer's disease, multi-infarct dementia, alcoholic dementia or other drug-related dementia, dementia associated with intracranial tumors or cerebral trauma, dementia associated with Huntington's disease or Parkinson's disease, or AIDS-related dementia; delirium; amnestic disorder; post-traumatic stress disorder; mental retardation; a learning disorder, for example reading disorder, mathematics disorder, or a disorder of written expression; attention-deficit/hyperactivity disorder; and age-related cognitive decline; and wherein the psychiatric disorder is selected from the group consisting of schizophrenia, for example of the paranoid, disorganized, catatonic, undifferentiated, or residual type; schizophreniform disorder; schizoaffective disorder, for example of the delusional type or the depressive type; delusional disorder; substance-induced psychotic disorder, for example psychosis induced by alcohol, amphetamine, *cannabis*, cocaine, hallucinogens, inhalants, opioids, or phencyclidine; personality disorder of the paranoid type; and personality disorder of the schizoid type; and wherein the drug addiction is an alcohol, amphetamine, cocaine, or opiate addiction.

The compounds of formula (I) or pharmaceutically acceptable salts thereof may be used as the sole active ingredient or in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefore, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

The present invention provides a method of treating a mammal, including a human, suffering from a neurodegenerative disorder selected from a cognition disorder or movement disorder, which method comprises administering to the subject a therapeutically effective amount of a compound of formula (I).

This invention further provides a method of treating a neurodegenerative disorder or condition in a mammal, including a human, which method comprises administering to said mammal an amount of a compound of formula (I) effective in inhibiting PDE1.

This invention also provides a method of treating a subject suffering from a psychiatric disorder, which method comprises administering to the subject a therapeutically effective amount of a compound of formula (I). Examples of psychiatric disorders that can be treated according to the present invention include, but are not limited to, Attention Deficit Hyperactivity Disorder (ADHD) schizophrenia, for example of the paranoid, disorganized, catatonic, undifferentiated, or residual type; schizophreniform disorder; schizoaffective disorder, for example of the delusional type or the depressive type; delusional disorder; substance-induced psychotic disorder, for example psychosis induced by alcohol, amphetamine, *cannabis*, cocaine, hallucinogens, inhalants, opioids, or phencyclidine; personality disorder of the paranoid type; and personality disorder of the schizoid type; and the anxiety disorder is selected from panic disorder; agoraphobia; a specific phobia; social phobia; obsessive-compulsive disorder; post-traumatic stress disorder; acute stress disorder; and generalized anxiety disorder.

It has been found that the compounds of formula (I) or pharmaceutically acceptable salts thereof may advantageously be administered in combination with at least one neuroleptic agent (which may be a typical or an atypical antipsychotic agent) to provide improved treatment of psychiatric disorders such as schizophrenia. The combinations, uses and methods of treatment of the invention may also provide advantages in treatment of patients who fail to respond adequately or who are resistant to other known treatments.

The present invention thus provides a method of treating a mammal suffering from a psychiatric disorder, such as schizophrenia, which method comprises administering to the mammal a therapeutically effective amount of a compound of formula (I), either alone or as combination therapy together with at least one neuroleptic agent.

The term "neuroleptic agent" as used herein refers to drugs, which have the effect on cognition and behaviour of antipsychotic agent drugs that reduce confusion, delusions, hallucinations, and psychomotor agitation in patients with psychoses. Also known as major tranquilizers and antipsychotic drugs, neuroleptic agents include, but are not limited to: typical antipsychotic drugs, including phenothiazines, further divided into the aliphatics, piperidines, and piperazines, thioxanthenes (e.g., cisordinol), butyrophenones (e.g., haloperidol), dibenzoxazepines (e.g., loxapine), dihydroindolones (e.g., molindone), diphenylbutylpiperidines (e.g., pimozide), and atypical antipsychotic drugs, including benzisoxazoles (e.g., risperidone), sertindole, olanzapine, quetiapine, osanetant and ziprasidone.

Particularly preferred neuroleptic agents for use in the invention are sertindole, olanzapine, risperidone, quetiapine, aripiprazole, haloperidol, clozapine, ziprasidone and osanetant.

The present invention further provides a method of treating a subject suffering from a cognition disorder, which method comprises administering to the subject a therapeutically effective amount of a compound of formula (I). Examples of cognition disorders that can be treated according to the present invention include, but are not limited to, Alzheimer's disease, multi-infarct dementia, alcoholic dementia or other drug-related dementia, dementia associated with intracranial tumors or cerebral trauma, dementia associated with Huntington's disease or Parkinson's disease, or AIDS-related dementia; delirium; amnestic disorder; post-traumatic stress disorder; mental retardation; a learning disorder, for example reading disorder, mathematics disorder, or a disorder of written expression; attention-deficit/hyperactivity disorder; and age-related cognitive decline.

This invention also provides a method of treating a movement disorder, which method comprises administering to the subject a therapeutically effective amount of a compound of formula (I). Examples of movement disorders that can be treated according to the present invention include, but are not limited to, Huntington's disease and dyskinesia associated with dopamine agonist therapy. This invention further provides a method of treating a movement disorder selected from Parkinson's disease and restless leg syndrome, which comprises administering to the subject a therapeutically effective amount of a compound of formula (I).

This invention also provides a method of treating a mood disorder, which method comprises administering to the subject a therapeutically effective amount of a compound of formula (I). Examples of mood disorders and mood episodes that can be treated according to the present invention include, but are not limited to, major depressive episode of the mild, moderate or severe type, a manic or mixed mood episode, a hypomanic mood episode; a depressive episode with a typical features; a depressive episode with melancholic features; a depressive episode with catatonic features; a mood episode with postpartum onset; post-stroke depression; major depressive disorder; dysthymic disorder; minor depressive disorder; premenstrual dysphoric disorder; post-psychotic depressive disorder of schizophrenia; a major depressive disorder superimposed on a psychotic disorder such as delusional disorder or schizophrenia; a bipolar disorder, for example bipolar I disorder, bipolar II disorder, and cyclothymic disorder. It is understood that a mood disorder is a psychiatric disorder.

This invention further provides a method of treating a disorder comprising as a symptom a deficiency in attention and/or cognition in a mammal, including a human, which method comprises administering to said mammal an amount of a compound of formula (I) effective in treating said disorder.

Other disorders that can be treated according to the present invention are obsessive/compulsive disorders, Tourette's syndrome and other tic disorders.

As used herein, and unless otherwise indicated, a "neurodegenerative disorder or condition" refers to a disorder or condition that is caused by the dysfunction and/or death of neurons in the central nervous system. The treatment of these disorders and conditions can be facilitated by administration of an agent which prevents the dysfunction or death of neurons at risk in these disorders or conditions and/or enhances the function of damaged or healthy neurons in such a way as to compensate for the loss of function caused by the dysfunction or death of at-risk neurons. The term "neurotrophic agent" as used herein refers to a substance or agent that has some or all of these properties.

Examples of neurodegenerative disorders and conditions that can be treated according to the present invention include, but are not limited to, Parkinson's disease; Huntington's disease; dementia, for example Alzheimer's disease, multi-infarct dementia, AIDS-related dementia, and Frontotemperal Dementia; neurodegeneration associated with cerebral trauma; neurodegeneration associated with stroke, neurodegeneration associated with cerebral infarct; hypoglycemia-induced neurodegeneration; neurodegeneration associated with epileptic seizure; neurodegeneration associated with neurotoxin poisoning; and multi-system atrophy In one embodiment of the present invention, the neurodegenerative disorder or condition involves neurodegeneration of striatal medium spiny neurons in a mammal, including a human.

In a further embodiment of the present invention, the neurodegenerative disorder or condition is Huntington's disease.

All references, including publications, patent applications and patents, cited herein are hereby incorporated by reference in their entirety and to the same extent as if each reference were individually and specifically indicated to be incorporated by reference and were set forth in its entirety (to the maximum extent permitted by law).

Headings and sub-headings are used herein for convenience only, and should not be construed as limiting the invention in any way.

The use of any and all examples, or exemplary language (including "for instance", "for example", "e.g.", and "as such") in the present specification is intended merely to better illuminate the invention, and does not pose a limitation on the scope of invention unless otherwise indicated.

The citation and incorporation of patent documents herein is done for convenience only, and does not reflect any view of the validity, patentability and/or enforceability of such patent documents.

The present invention includes all modifications and equivalents of the subject-matter recited in the claims appended hereto, as permitted by applicable law.

COMPOUNDS OF THE INVENTION

TABLE 1

Compounds of the invention

| Compound number | Compound name | PDE1A IC50 (nM) | PDE1B IC50 (nM) | PDE1C IC50 (nM) |
| --- | --- | --- | --- | --- |
| 1 Stereoisomer 1 | 8-fluoro-7-methoxy-N-(3-methyltetrahydrofuran-3-yl)quinazolin-4-amine | 50 | 9.9 | 28 |
| 1 Stereoisomer 2 | 8-fluoro-7-methoxy-N-(3-methyltetrahydrofuran-3-yl)quinazolin-4-amine | 250 | 65 | 260 |
| 2 Stereoisomer 1 | 8-fluoro-7-methoxy-N-methyl-N-(tetrahydrofuran-3-yl)quinazolin-4-amine | 1100 | 300 | 1300 |
| 2 Stereoisomer 2 | 8-fluoro-7-methoxy-N-methyl-N-(tetrahydrofuran-3-yl)quinazolin-4-amine | 100 | 18 | 76 |
| 3 Stereoisomer 1 | 8-fluoro-7-methoxy-N-(2-methyltetrahydrofuran-3-yl)quinazolin-4-amine | 1900 | 650 | 1800 |
| 3 Stereoisomer 2 | 8-fluoro-7-methoxy-N-(2-methyltetrahydrofuran-3-yl)quinazolin-4-amine | 420 | 87 | 260 |
| 3 Stereoisomer 3 | 8-fluoro-7-methoxy-N-(2-methyltetrahydrofuran-3-yl)quinazolin-4-amine | 530 | 70 | 310 |
| 3 Stereoisomer 4 | 8-fluoro-7-methoxy-N-(2-methyltetrahydrofuran-3-yl)quinazolin-4-amine | 600 | 120 | 410 |
| 4 Stereoisomer 1 | 8-chloro-7-methoxy-N-(tetrahydrofuran-3-yl)quinazolin-4-amine | 790 | 310 | 200 |
| 4 Stereoisomer 2 | 8-chloro-7-methoxy-N-(tetrahydrofuran-3-yl)quinazolin-4-amine | 190 | 45 | 33 |
| 5 stereoisomer 1 | 8-chloro-7-methoxy-N-(2-methyltetrahydrofuran-3-yl)quinazolin-4-amine | 300 | 49 | 27 |

TABLE 1-continued

Compounds of the invention

| Compound number | Compound name | PDE1A IC50 (nM) | PDE1B IC50 (nM) | PDE1C IC50 (nM) |
|---|---|---|---|---|
| 5 stereoisomer 2 | 8-chloro-7-methoxy-N-(2-methyltetrahydrofuran-3-yl)quinazolin-4-amine | 230 | 37 | 35 |
| 5 stereoisomer 3 | 8-chloro-7-methoxy-N-(2-methyltetrahydrofuran-3-yl)quinazolin-4-amine | 1500 | 460 | 250 |
| 5 stereoisomer 4 | 8-chloro-7-methoxy-N-(2-methyltetrahydrofuran-3-yl)quinazolin-4-amine | 450 | 58 | 36 |
| 6 stereoisomer 1 | 8-chloro-7-methoxy-N-methyl-N-(tetrahydrofuran-3-yl)quinazolin-4-amine | 1800 | 330 | 140 |
| 6 stereoisomer 2 | 8-chloro-7-methoxy-N-methyl-N-(tetrahydrofuran-3-yl)quinazolin-4-amine | 150 | 15 | 11 |
| 7 stereoisomer 2 | 8-chloro-7-methoxy-N-(3-methyltetrahydrofuran-3-yl)quinazolin-4-amine | 490 | 75 | 48 |
| 7 stereoisomer 1 | 8-chloro-7-methoxy-N-(3-methyltetrahydrofuran-3-yl)quinazolin-4-amine | 200 | 23 | 11 |
| 8 Stereoisomer 1 | cis-4-(8-fluoro-7-methoxyquinazolin-4-yl)hexahydro-2H-furo[3,2-b]pyrrole | 72 | 21 | 60 |
| 8 Stereoisomer 2 | cis-4-(8-fluoro-7-methoxyquinazolin-4-yl)hexahydro-2H-furo[3,2-b]pyrrole | 4034 | 2200 | 2500 |
| 9 Stereoisomer 1 | cis-4-(8-chloro-7-methoxyquinazolin-4-yl)hexahydro-2H-furo[3,2-b]pyrrole | 156 | 40 | 23 |
| 9 Stereoisomer 2 | cis-4-(8-chloro-7-methoxyquinazolin-4-yl)hexahydro-2H-furo[3,2-b]pyrrole | 2260 | 1200 | 550 |
| 10 Stereoisomer 1 | cis-4-(8-bromo-7-methoxyquinazolin-4-yl)hexahydro-2H-furo[3,2-b]pyrrole | 147 | 49 | 11 |
| 10 Stereoisomer 2 | cis-4-(8-bromo-7-methoxyquinazolin-4-yl)hexahydro-2H-furo[3,2-b]pyrrole | 10% | 47% | 210 |
| 11 Stereoisomer 1 | 8-chloro-7-methoxy-N-methyl-N-(3-methyltetrahydrofuran-3-yl)quinazolin-4-amine | 292 | 65 | 33 |
| 11 Stereoisomer 2 | 8-chloro-7-methoxy-N-methyl-N-(3-methyltetrahydrofuran-3-yl)quinazolin-4-amine | 152 | 31 | 15 |
| 12 Stereoisomer 1 | 8-chloro-N-(2,3-dimethyltetrahydrofuran-3-yl)-7-methoxyquinazolin-4-amine | 853 | 200 | 130 |
| 12 Stereoisomer 2 | 8-chloro-N-(2,3-dimethyltetrahydrofuran-3-yl)-7-methoxyquinazolin-4-amine | 286 | 65 | 38 |
| 12 Stereoisomer 3 | 8-chloro-N-(2,3-dimethyltetrahydrofuran-3-yl)-7-methoxyquinazolin-4-amine | 145 | 21 | 14 |
| 12 Stereoisomer 4 | 8-chloro-N-(2,3-dimethyltetrahydrofuran-3-yl)-7-methoxyquinazolin-4-amine | 76 | 7 | 4 |

TABLE 1-continued

Compounds of the invention

| Compound number | Compound name | PDE1A IC50 (nM) | PDE1B IC50 (nM) | PDE1C IC50 (nM) |
|---|---|---|---|---|
| 13 Stereoisomer 1 | 8-chloro-N-(2,3-dimethyltetrahydrofuran-3-yl)-7-methoxy-N-methylquinazolin-4-amine | 2550 | 410 | 200 |
| 13 Stereoisomer 2 | 8-chloro-N-(2,3-dimethyltetrahydrofuran-3-yl)-7-methoxy-N-methylquinazolin-4-amine | 207 | 34 | 17 |
| 13 Stereoisomer 3 | 8-chloro-N-(2,3-dimethyltetrahydrofuran-3-yl)-7-methoxy-N-methylquinazolin-4-amine | 85 | 7 | 5 |
| 13 Stereoisomer 4 | 8-chloro-N-(2,3-dimethyltetrahydrofuran-3-yl)-7-methoxy-N-methylquinazolin-4-amine | 300 | 26 | 13 |
| 14 Stereoisomer 1 | 8-chloro-7-methoxy-N-methyl-N-(2-methyltetrahydrofuran-3-yl)quinazolin-4-amine | 2642 | 510 | 200 |
| 14 Stereoisomer 2 | 8-chloro-7-methoxy-N-methyl-N-(2-methyltetrahydrofuran-3-yl)quinazolin-4-amine | 170 | 18 | 10 |
| 14 Stereoisomer 3 | 8-chloro-7-methoxy-N-methyl-N-(2-methyltetrahydrofuran-3-yl)quinazolin-4-amine | 1532 | 490 | 200 |
| 14 Stereoisomer 4 | 8-chloro-7-methoxy-N-methyl-N-(2-methyltetrahydrofuran-3-yl)quinazolin-4-amine | 285 | 30 | 14 |
| 15 Stereoisomer 1 | 8-fluoro-7-methoxy-N-methyl-N-(3-methyltetrahydrofuran-3-yl)quinazolin-4-amine | 688 | 110 | 320 |
| 15 Stereoisomer 2 | 8-fluoro-7-methoxy-N-methyl-N-(3-methyltetrahydrofuran-3-yl)quinazolin-4-amine | 333 | 47 | 81 |
| 16 Stereoisomer 1 | 8-fluoro-7-methoxy-N-(tetrahydrofuran-3-yl)quinazolin-4-amine | 1180 | 430 | 1200 |
| 16 Stereoisomer 2 | 8-fluoro-7-methoxy-N-(tetrahydrofuran-3-yl)quinazolin-4-amine | 315 | 81 | 230 |
| 17 Stereoisomer 3 | N-(2,3-dimethyltetrahydrofuran-3-yl)-8-fluoro-7-methoxyquinazolin-4-amine | 451 | 100 | 390 |
| 17 Stereoisomer 2 | N-(2,3-dimethyltetrahydrofuran-3-yl)-8-fluoro-7-methoxyquinazolin-4-amine | 73 | 5 | 22 |
| 17 Stereoisomer 4 | N-(2,3-dimethyltetrahydrofuran-3-yl)-8-fluoro-7-methoxyquinazolin-4-amine | 408 | 140 | 440 |
| 17 Stereoisomer 1 | N-(2,3-dimethyltetrahydrofuran-3-yl)-8-fluoro-7-methoxyquinazolin-4-amine | 184 | 27 | 98 |
| 18 Stereoisomer 2 | 8-fluoro-7-methoxy-N-methyl-N-(2-methyltetrahydrofuran-3-yl)quinazolin-4-amine | 2467 | 550 | 1400 |
| 18 Stereoisomer 1 | 8-fluoro-7-methoxy-N-methyl-N-(2-methyltetrahydrofuran-3-yl)quinazolin-4-amine | 1732 | 510 | 1100 |

TABLE 1-continued

Compounds of the invention

| Compound number | Compound name | PDE1A IC50 (nM) | PDE1B IC50 (nM) | PDE1C IC50 (nM) |
|---|---|---|---|---|
| 18 Stereoisomer 3 | 8-fluoro-7-methoxy-N-methyl-N-(2-methyltetrahydrofuran-3-yl)quinazolin-4-amine | 200 | 47 | 87 |
| 18 Stereoisomer 4 | 8-fluoro-7-methoxy-N-methyl-N-(2-methyltetrahydrofuran-3-yl)quinazolin-4-amine | 515 | 60 | 120 |
| 19 Stereoisomer 1 | N-(2,3-dimethyltetrahydrofuran-3-yl)-8-fluoro-7-methoxy-N-methylquinazolin-4-amine | 229 | 32 | 86 |
| 19 Stereoisomer 2 | N-(2,3-dimethyltetrahydrofuran-3-yl)-8-fluoro-7-methoxy-N-methylquinazolin-4-amine | 185 | 32 | 55 |
| 19 Stereoisomer 3 | N-(2,3-dimethyltetrahydrofuran-3-yl)-8-fluoro-7-methoxy-N-methylquinazolin-4-amine | 2487 | 420 | 1200 |
| 19 Stereoisomer 4 | N-(2,3-dimethyltetrahydrofuran-3-yl)-8-fluoro-7-methoxy-N-methylquinazolin-4-amine | 97 | 10 | 34 |

EXPERIMENTAL SECTION
Preparation of the Compounds of the Invention

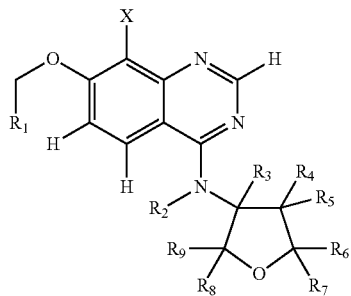

Compounds of the general formula I of the invention may be prepared as described in the following reaction schemes. Unless otherwise indicated, in the reaction schemes and discussion that follow, $R_1$-$R_{10}$, and X are as defined above. Scheme 1 below depicts a coupling reaction between a compound of formula II and a derivative of 3-amino tetrahydrofurane of formula III, to generate the substituted halogenated quinazolin-THF-amine compounds of formula I.

Scheme 1

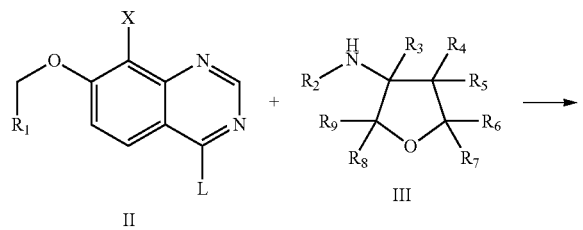

L is a leaving group, e.g. Cl, Br, I, methanesulfonyl, 4-toluenesulfonyl. This reaction is typically carried out in a solvent such as, for example, toluene, optionally in the presence of a carbonate base, at a temperature range of from about 0° C. to about 200° C. Other suitable solvents include benzene, chloroform, dioxane, ethyl acetate, 2-propanol and xylene. Alternatively, solvent mixtures such as toluene/2-propanol can be used. Preferably the reactants are heated under reflux in DMSO or DMF for a period of from about 2 hours to about 24 hours, optionally using a microwave oven.

The reaction depicted in Scheme 1 can also conveniently be carried out in a palladium-catalyzed fashion. Typically, a mixture of a compound of formula II, a compound of formula III and a palladium (II) source such as Pd(OAc)$_2$ or Pd$_2$(dba)$_3$ is heated in a convenient solvent such as toluene in the presence of a bisphosphine ligand, such as 2,2'-bis(diphenylphosphino)-1,1'-binaphthyl "BINAP", and an alkoxide base such as sodium tert-butoxide. The reaction mixture is stirred at 100° C. for 7 hr, followed by purification of the product by preparative HPLC to obtain the desired product.

Starting materials of formula II i.e. quinazolines are either commercially available or can be prepared as described in the literature e.g. Dechantsreiter, Michael A. et al From PCT Int. Appl., 2013192345, 27 Dec. 2013, Armarego, Wilfred L. F. and Reece, Phillip A. Australian Journal of Chemistry, 34(7), 1561-6; 1981, or as described in this patent application.

Starting materials of formula III are either commercially available or can be prepared by methods analogues to those described in the literature e.g. Wipf, Peter; Manojlovic, Marija D. Beilstein Journal of Organic Chemistry (2011), 7, 824-830, Yoshimitsu, Y. et al. Journal of Organic Chemistry (2010), 75(11), 3843-3846, Shiau, T. P. et al. Bioorganic & Medicinal Chemistry Letters (2009), 19(4), 1110-1114.

Compounds of formula I, wherein R2 is not hydrogen, can be prepared by the alkylation of a compounds of formula IV, wherein R2 is hydrogen, with an alkyl halide of formula V as shown in scheme 2.

Scheme 2

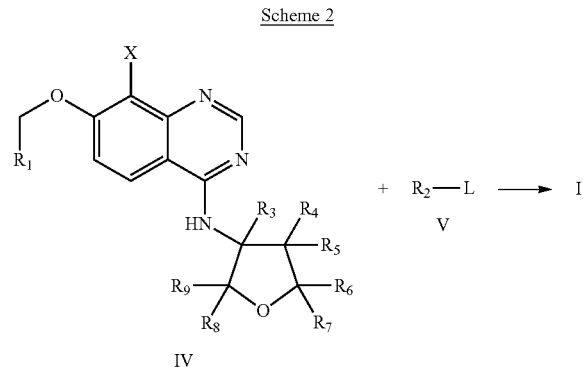

This reaction is typically carried out in a suitable solvent, such as dimethylformamide, dimethylacetamide, tetrahydrofuran or acetonitrile, in the presence of a suitable base such as a carbonate base, e.g. potassium carbonate, or a tertiary amine base, e.g. triethylamine or diisopropylethylamine, or a strong base such as sodium hydride at a temperature ranging from about 0° C. to about 100° C.

The invention disclosed herein is further illustrated by the following non-limiting examples.

General Methods

Analytical LC-MS data were obtained using the methods identified below.

Method 1:

An Agilent 1200 LCMS system with ELS detector was used. Column: Agilent TC-C18 5 μm; 2.1×50 mm; Column temperature: 50° C.; Solvent system: A=water/trifluoroacetic acid (99.9:0.1) and B=acetonitrile/trifluoroacetic acid (99.95:0.05); Method: Linear gradient elution with A:B=99:1 to 0:100 in 4.0 minutes and with a flow rate of 0.8 mL/minute.

Method 2:

An Agilent 1200 LCMS system with ELS detector was used. Column: XBridge ShieldRP18, 5 μm, 50×2.1 mm; Column temperature: 40° C.; Solvent system: A=water/NH$_3$*H2O (99.95:0.05) and B=acetonitrile; Method: Linear gradient elution with A:B=95:5 to 0:100 in 3.4 minutes and with a flow rate of 0.8 mL/minute.

Method 3:

An Agilent 1200 LCMS system with ELS detector was used. Column: XBridge ShieldRP18, 5 μm, 50×2.1 mm; Column temperature: 40° C.; Solvent system: A=water/NH$_3$*H2O (99.95:0.05) and B=acetonitrile; Method: Linear gradient elution with A:B=99:1 to 0:100 in 3.4 minutes and with a flow rate of 0.8 mL/minute.

Method 4:

An Agilent 1100 LCMS system with ELS detector was used. Column: YMC ODS-AQ, 5 μm, 50×2.0 mm; Column temperature: 50° C.; Solvent system: A=0.1% TFA in water and B=0.05% TFA in Acetonitrile; Method: Linear gradient elution with A:B=99:1 to 5:95 in 3.5 minutes and with a flow rate of 0.8 mL/minute.

Method 5:

An Agilent 1200 LCMS system with ELS detector was used. Column: Agilent TC-C18 5 μm; 2.1×50 mm; Column temperature: 50° C.; Solvent system: A=water/trifluoroacetic acid (99.9:0.1) and B=acetonitrile/trifluoroacetic acid (99.95:0.05); Method: Linear gradient elution with A:B=90:10 to 0:100 in 4.0 minutes and with a flow rate of 0.8 mL/min.

Preparative LC-MS-purification was performed on a PE Sciex API 150EX instrument with atmospheric pressure chemical ionization. Column: 50×20 mm YMC ODS-A with 5 μm particle size; Solvent system: A=water/trifluoroacetic acid (99.965:0.035) and B=acetonitrile/water/trifluoroacetic acid (94.965:5:0.035); Method: Linear gradient elution with A:B=80:20 to 0:100 in 7 minutes and with a flow rate of 22.7 mL/minute. Fraction collection was performed by split-flow MS detection.

Preparative SFC was performed on a Thar 80 instrument. Exemplified conditions can be, but not limited to: Column AD 250×30 mm with 20 μm particle size; Column temperature: 38° C., Mobile phase: Supercritical CO$_2$/EtOH (0.2% NH$_3$H$_2$O)=45/55.

Synthesis of Intermediate I

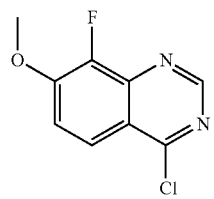

4-Chloro-8-fluoro-7-methoxyquinazoline

Step 1:

Commercial available (CAS 1180497-45-3) 2-amino-3-fluoro-4-methoxybenzoic acid (8 g, 43.21 mmol) and ammonium acetate (67 g, 864 mol) in trimethoxymethane (250 mL) were stirred at 100° C. for 12 hrs. The mixture was filtered and washed with water (3×20 mL), the white solid was dried under vacuum to give 8-fluoro-7-methoxyquinazolin-4(3H)-one (8 g, 95%).

Step 2:

To a mixture of 8-fluoro-7-methoxyquinazolin-4(3H)-one (4.0 g, 20.6 mmol) and diisopropylethylamine (11 g, 82 mmol) in toluene (100 mL) was added POCl$_3$ (6.32 g, 41.2 mmol) at 0° C. The reaction was stirred at 100° C. for 12 hrs. The mixture was then cooled to 20° C. and poured into ice-water (100 mL). The water phase was extracted with dichloromethane (3×100 mL). The combined organic phases were washed with brine (3×10 mL) and concentrated under vacuum. The residue was purified by flash chromatography on silica gel using a gradient of ethyl acetate and petroleum ether to give 4-chloro-8-fluoro-7-methoxyquinazoline 3 g (70%).

Example 1

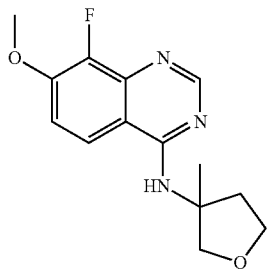 [SMILES: COc1ccc2c(NC3(C)CCOC3)ncnc2c1F]

8-Fluoro-7-methoxy-N-(3-methyltetrahydrofuran-3-yl)quinazolin-4-amine

A mixture of 4-chloro-8-fluoro-7-methoxyquinazoline (560 mg, 2.63 mmol), (+/−)-3-methyltetrahydrofuran-3-amine hydrochloride (400 mg, 2.92 mmol) and $K_2CO_3$ (800 mg, 5.84 mmol) in DMSO (30 mL) was stirred at 100° C. for 12 hours. The solution was then poured into ice-water (100 mL) and extracted with dichloromethane (3×50 mL). The combined organic phases were washed with brine (3×10 mL), dried over $MgSO_4$ and concentrated under vacuum. The residue was purified by flash chromatography on silica gel using a gradient of ethyl acetate and petroleum ether to give (+/−)-8-fluoro-7-methoxy-N-(3-methyltetrahydrofuran-3-yl)quinazolin-4-amine 320 mg (44%).

The racemic mixture (320 mg) was purified by SFC (Column: AY (250 mm*30 mm, 5 um)) separation and numbered according to the order of elution:
Stereoisomer 1 (First Eluting by SFC): 140 mg
$^1$H NMR (CDCl$_3$, 400 MHz): δ 8.66 (s, 1H), 7.44 (d, J=8.8 Hz, 1H), 7.19 (t, J=8.4 Hz, 1H), 5.68 (s, 1H), 4.16 (d, J=9.2 Hz, 1H), 4.05 (s, 3H), 4.02~3.98 (m, 2H), 3.87 (d, J=9.2 Hz, 1H), 2.66~2.60 (m, 1H), 2.17~2.09 (m, 1H), 1.75 (s, 3H).
LC-MS: (m/z) 278.1 (MH+) $t_R$ (minutes, method 1)=1.84 minutes.
$[α]^{20}_D$=18° (c=0.1 mg/mL, methanol).
Stereoisomer 2 (Second Eluting by SFC): 160 mg
$^1$H NMR (CDCl$_3$, 400 MHz): δ 8.66 (s, 1H), 7.44 (dd, J=8.8, 1.6 Hz, 1H), 7.19 (t, J=8.4 Hz, 1H), 5.70 (s, 1H), 4.16 (d, J=9.2 Hz, 1H), 4.05 (s, 3H), 4.02~3.98 (m, 2H), 3.87 (d, J=9.2 Hz, 1H), 2.66~2.60 (m, 1H), 2.16~2.09 (m, 1H), 1.75 (s, 3H).
LC-MS: (m/z) 278.1 (MH+) $t_R$ (minutes, method 1)=1.84 minutes.
$[α]^{20}_D$=−26° (c=0.1 mg/mL, methanol)

Example 2

8-Fluoro-7-methoxy-N-methyl-N-(tetrahydrofuran-3-yl)quinazolin-4-amine

Step 1:
A solution of 4-chloro-8-fluoro-7-methoxyquinazoline (440 mg, 2.06 mmol), tetrahydrofuran-3-amine (200 mg, 2.29 mmol) and diisopropylethylamine (600 mg, 4.58 mmol) in DMF (30 mL) was stirred at 100° C. for 12 hrs. The solution was concentrated under vacuum, and the residue was purified by flash chromatography on silica gel using a gradient of ethyl acetate and petroleum ether to give 8-fluoro-7-methoxy-N-(tetrahydrofuran-3-yl)quinazolin-4-amine 500 mg (83%) as a white solid. Step 2: To a solution of 8-fluoro-7-methoxy-N-(tetrahydrofuran-3-yl)quinazolin-4-amine (480 mg, 1.83 mmol) in THF (20 mL) was added a 60% suspension of NaH in mineral oil (100 mg, 2.74 mmol) at 0° C., then it was stirred at 0° C. for 30 min and then allowed to warm to room temperature. Methyliodide (388 mg, 2.74 mmol) was added at 20° C. and the reaction was stirred at 20° C. for 12 hrs. The solution was quenched with sat. aq. NH$_4$Cl (2 mL), then concentrated under vacuum. The residue was diluted with dichloromethane (100 mL), washed with brine (3×10 mL), dried over MgSO$_4$ and concentrated under vacuum. The crude product was purified by flash chromatography on silica gel using a gradient of ethyl acetate and petroleum ether to give 8-fluoro-7-methoxy-N-methyl-N-(tetrahydrofuran-3-yl)quinazolin-4-amine 230 mg (46%).

The mixture of stereoisomers (230 mg) was purified by SFC (Column: AD-H (250 mm*30 mm, 5 um)) separation and numbered according to the order of elution:
Stereoisomer 1 (First Eluting by SFC): 75 mg
$^1$H NMR (CDCl$_3$, 400 MHz): δ 8.66 (s, 1H), 7.77~7.74 (m, 1H), 7.19~7.15 (m, 1H), 5.29~5.23 (m, 1H), 4.17~4.12 (m, 1H), 4.07 (s, 3H), 3.99 (d, J=5.6 Hz, 2H), 3.75 (q, J=7.6 Hz, 1H), 3.32 (s, 3H), 2.49~2.44 (m, 1H), 2.12~2.08 (m, 1H).
LC-MS: (m/z) 278.1 (MH+) $t_R$ (minutes, method 1)=1.78 minutes.
$[α]^{20}_D$=−15° (c=(0.1 mg/mL, methanol)
Stereoisomer 2 (Second Eluting by SFC): 80 mg
$^1$H NMR (CDCl$_3$, 400 MHz): δ 8.66 (s, 1H), 7.76 (dd, J=9.2, 2.0 Hz, 1H), 7.18 (dd, J=9.2, 8.0 Hz, 1H), 5.31~5.23 (m, 1H), 4.17~4.12 (m, 1H), 4.06 (s, 3H), 3.99 (d, J=5.6 Hz, 2H), 3.75 (q, J=7.6 Hz, 1H), 3.32 (s, 3H), 2.48~2.44 (m, 1H), 2.12~2.08 (m, 1H).
LC-MS: (m/z) 278.1 (MH+) $t_R$ (minutes, method 1)=1.79 minutes.
$[α]^{20}_D$=16° (c=0.1 mg/mL, methanol)

Example 3

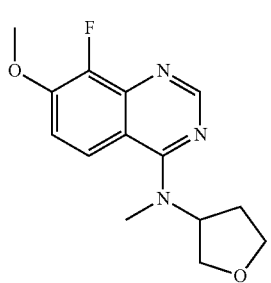 [SMILES: COc1ccc2c(N(C)C3CCOC3)ncnc2c1F]

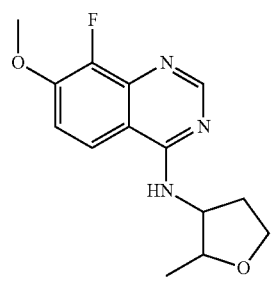 [SMILES: COc1ccc2c(NC3CCOC3C)ncnc2c1F]

8-Fluoro-7-methoxy-N-(2-methyltetrahydrofuran-3-yl)quinazolin-4-amine

A solution of 4-chloro-8-fluoro-7-methoxyquinazoline (500 mg, 2.35 mmol), 2-methyltetrahydrofuran-3-amine hydrochloride (388 mg, 2.82 mmol) and diisopropylethylamine (607 mg, 4.70 mmol) in DMF (20 mL) was stirred at 100° C. for hours. The solution was concentrated under vacuum, and the residue was purified by flash chromatography on silica gel using a gradient of ethyl acetate and petroleum ether to give a 8-fluoro-7-methoxy-N-(2-methyltetrahydrofuran-3-yl)quinazolin-4-amine as a mixture of all four possible stereoisomers 600 mg (84%).

The mixture of stereoisomers (600 mg) was purified by SFC (Column: AD (250 mm*30 mm, 5 um)) separation and numbered according to the order of elution:

Stereoisomer 1 (First Eluting by SFC): 180 mg
$^1$H NMR (CDCl$_3$, 400 MHz): δ 8.66 (s, 1H), 7.47 (dd, J=8.8, 1.2 Hz, 1H), 7.21 (t, J=8.8 Hz, 1H), 5.72 (d, J=6.8 Hz, 1H), 4.64-4.58 (m, 1H), 4.09-3.98 (m, 6H), 2.59-2.50 (m, 1H), 2.00-1.96 (m, 1H), 1.36 (d, J=6.4 Hz, 3H).
LC-MS: (m/z) 278.1 (MH+) t$_R$ (minutes, method 1)=1.84 minutes.
[α]$^{20}_D$=−23° (c=0.1 mg/mL, methanol)

Stereoisomer 2 (Second Eluting by SFC): 80 mg
$^1$H NMR (CDCl$_3$, 400 MHz): δ 8.65 (s, 1H), 7.48 (dd, J=9.2, 1.6 Hz, 1H), 7.24-7.20 (m, 1H), 5.68 (d, J=8.4 Hz, 1H), 5.07-5.02 (m, 1H), 4.11-4.01 (m, 5H), 3.85-3.82 (m, 1H), 2.56-2.50 (m, 1H), 2.03-1.99 (m, 1H), 1.26 (d, J=6.0 Hz, 3H).
LC-MS: (m/z) 278.1 (MH+) t$_R$ (minutes, method 1)=1.82 minutes.
[α]$^{20}_D$=22° (c=0.1 mg/mL, methanol)

Stereoisomer 3 (Third Eluting by SFC): 180 mg
$^1$H NMR (CDCl$_3$, 400 MHz): δ 8.64 (s, 1H), 7.48 (dd, J=9.2, 1.6 Hz, 1H), 7.24-7.19 (m, 1H), 5.71 (d, J=8.4 Hz, 1H), 5.07-5.02 (m, 1H), 4.11-4.01 (m, 5H), 3.85-3.82 (m, 1H), 2.56-2.50 (m, 1H), 2.03-1.97 (m, 1H), 1.26 (d, J=6.4 Hz, 3H).
LC-MS: (m/z) 278.1 (MH+) t$_R$ (minutes, method 1)=1.81 minutes.
[α]$^{20}_D$=−2 1° (c=0.1 mg/mL, methanol)

Stereoisomer 4 (Fourth Eluting by SFC): 80 mg
$^1$H NMR (CDCl$_3$, 400 MHz): δ 8.66 (s, 1H), 7.47 (dd, J=8.8, 1.2 Hz, 1H), 7.21 (t, J=8.8 Hz, 1H), 5.72 (d, J=7.2 Hz, 1H), 4.64-4.60 (m, 1H), 4.09-3.98 (m, 6H), 2.59-2.50 (m, 1H), 2.00-1.93 (m, 1H), 1.36 (d, J=6.4 Hz, 3H).
LC-MS: (m/z) 278.1 (MH+) t$_R$ (minutes, method 1)=1.85 minutes.
[α]$^{20}_D$=34° (c=0.1 mg/mL, methanol)

Synthesis of Intermediate II

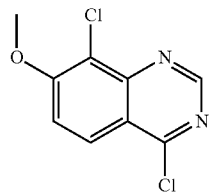

4,8-dichloro-7-methoxyquinazoline

Step 1:
To the suspension of commercial available (CAS 33234-36-5) 2-chloro-3-methoxybenzoic acid (19.5 g, 104 mmol) in acetic acid (100 mL) and H$_2$O (100 mL) at room temperature was added bromine (10.8 mL, 209 mmol) dropwise. The resulting mixture was heated at 60° C. overnight. Then cooled to room temperature and extracted with dichloromethane (3×200 mL). The combined organic phases were washed with water (3×300 mL), dried over Na$_2$SO$_4$, filtered and concentrated to give 6-bromo-2-chloro-3-methoxybenzoic acid 23 g (83%).

Step 2:
To as suspension of 6-bromo-2-chloro-3-methoxybenzoic acid (10 g, 38 mmol) in toluene (200 mL) was added diphenylphosphoryl azide (12.2 mL, 56.6 mmol) triethylamine (15.8 mL, 113 mmol) and tert-butanol (18.0 ml, 188 mmol). The reaction mixture was heated at 100° C. for 2 hrs under N$_2$. The mixture was evaporated and the residue was diluted with ethyl acetate. The organic phase was washed with 5% aqueous citric acid solution, water, sat. aq. NaHCO$_3$, brine, dried over Na$_2$SO$_4$, and concentrated. The crude product was purified by flash chromatography on silica gel using a gradient of ethyl acetate and petroleum ether, yielding tert-butyl (6-bromo-2-chloro-3-methoxyphenyl)carbamate 12 g (95%).

Step 3:
To an ice-cold solution of tert-butyl (6-bromo-2-chloro-3-methoxyphenyl)carbamate (12 g, 37 mmol) in dichloromethane (150 mL) was added trifluoroacetic acid (20 mL). The mixture was warmed to room temperature and stirred for 5 hrs. The solution was then concentrated and the residue was diluted with dichloromethane, adjusted to pH=9 by sat. aq. NaHCO$_3$, washed with water, dried over Na$_2$SO$_4$, filtered and concentrated to give 6-bromo-2-chloro-3-methoxyaniline 8.3 g (98%).

Step 4:
To a solution of 6-bromo-2-chloro-3-methoxyaniline (8.3 g, 35 mmol) in methanol (300 mL) was added 1,3-bis(diphenylphosphino)propane (2.90 g, 7.02 mmol), Pd(AcO)$_2$ (1.58 g, 7.02 mmol) and triethylamine (4.89 mL, 35.1 mmol). The reaction mixture was stirred at 100° C. under an atmosphere of CO (3 MPa) for 2 days. The mixture was cooled to room temperature and filtered. The filtrate was concentrated and the residue was dissolved in dichloromethane. The resulting solution was washed with water, dried over Na$_2$SO$_4$, filtered and concentrated. The crude product was purified by flash chromatography on silica gel using a gradient of ethyl acetate and petroleum ether to yield methyl 2-amino-3-chloro-4-methoxybenzoate 5.0 g (65%).

Step 5:
To a solution of methyl 2-amino-3-chloro-4-methoxybenzoate (4.95 g, 23.0 mmol) in a mixture of THF (60 mL) and H$_2$O (30 mL) was added LiOH.H$_2$O (2.89 g, 68.8 mmol). The mixture was heated at 50° C. for 3 days. The mixture was then cooled to room temperature and extracted with ethyl acetate. The aqueous phase was acidified by aq. KHSO$_4$ until pH=3, filtered, and the filter cake was collected, washed with water and dried to give 2-amino-3-chloro-4-methoxybenzoic acid 3.2 g (69%).

Step 6:
To a solution of 2-amino-3-chloro-4-methoxybenzoic acid (700 mg, 3.47 mmol) in CH(OMe)$_3$ (40 mL) was added ammonium acetate (5.35 g, 69.4 mmol). The mixture was then heated at 90° C. overnight. The reaction was cooled to room temperature, filtered and the filter cake was collected, washed with water and dried to give 8-chloro-7-methoxy-quinazolin-4(3H)-one 630 mg (86%).

Step 7:

To an ice-cold solution of 8-chloro-7-methoxyquinazolin-4(3H)-one (630 mg, 2.99 mmol) in toluene (15 mL) was dropwise added POCl$_3$ (0.56 mL, 6.0 mmol) and diisopropylethylamine (2.08 mL, 12.0 mmol). The mixture was heated at 100° C. overnight, then cooled to room temperature and carefully poured into ice-water. The water phase was extracted with dichloromethane (2×30 mL). The combined organic phases were washed with water, dried over Na$_2$SO$_4$, filtered, concentrated in vacuo. The crude product was purified by flash chromatography on silica gel using a gradient of dichloromethane and ethyl acetate to give 4,8-dichloro-7-methoxyquinazoline 580 mg (85%).

Example 4

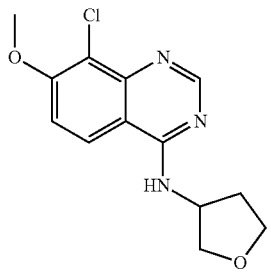 [SMILES: COc1ccc2c(NC3CCOC3)ncnc2c1Cl]

8-Chloro-7-methoxy-N-(tetrahydrofuran-3-yl)quinazolin-4-amine

To a solution of 4,8-dichloro-7-methoxyquinazoline (650 mg, 2.84 mmol) in dimethylformamide (20 mL) was added tetrahydrofuran-3-amine (297 mg, 3.41 mmol) and diisopropylethylamine (0.99 mL, 5.7 mmol). Through the mixture was bubbled N$_2$ for 5 minutes. The reaction was then heated at 100° C. for 3 hrs under an atmosphere of N$_2$. The crude mixture was concentrated and the residue was purified by flash chromatography on silica gel using a gradient of ethyl acetate and petroleum ether to give 8-chloro-7-methoxy-N-(tetrahydrofuran-3-yl)quinazolin-4-amine 650 mg (82%).

The racemic mixture (650 mg) was purified by SFC (Column: Chiral Pak AD 5 μm, Daicel Chemical Industries, Ltd, 250)(30 mm I.D.) separation and numbered according to the order of elution:

Stereoisomer 1 (First Eluting by SFC): 200 mg $^1$H NMR (CD$_3$OD, 400 MHz): δ 8.45 (s, 1H), 8.20 (d, J=9.29 Hz, 1H), 7.38 (d, J=9.29 Hz, 1H), 3.99~4.07 (m, 5H), 3.77~3.89 (m, 2H), 2.32~2.42 (m, 1H), 2.04~2.14 (m, 1H).

LC-MS: (m/z) 280.1 (MH+) t$_R$ (minutes, method 2)=1.58 minutes $[α]_D^{20}$+38.3° (c=0.10, methanol).

Stereoisomer 2 (Second Eluting by SFC): 200 mg $^1$H NMR (CD$_3$OD, 400 MHZ): δ 8.45 (s, 1H), 8.20 (d, J=9.29 Hz, 1H), 7.38 (d, J=9.05 Hz, 1H), 3.99~4.07 (m, 5H), 3.77~3.89 (m, 2H), 2.32~2.42 (m, 1H), 2.04~2.14 (m, 1H).

LC-MS: (m/z) 280.1 (MH+) t$_R$ (minutes, method 1)=1.57 minutes $[α]_D^{20}$−32.0° (c=0.10, methanol).

Example 5

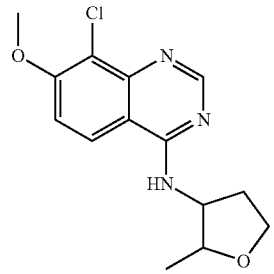 [SMILES: COc1ccc2c(NC3CCOC3C)ncnc2c1Cl]

8-Chloro-7-methoxy-N-(2-methyltetrahydrofuran-3-yl)quinazolin-4-amine

To a solution of 4,8-dichloro-7-methoxyquinazoline (450 mg, 1.96 mmol) in DMF (20 mL) was added 2-methyltetrahydrofuran-3-amine (mixture of all 4 stereoisomers) (322 mg, 2.36 mmol) and diisopropylethylamine (1.03 mL, 5.89 mmol). Through the mixture was bubbled N$_2$ for 5 minutes and it was then heated at 100° C. overnight. The crude mixture was concentrated and the residue was purified by flash chromatography on silica gel using a gradient of ethyl acetate and petroleum ether to yield 8-chloro-7-methoxy-N-(2-methyltetrahydrofuran-3-yl)quinazolin-4-amine 450 mg (78%) as a mixture of all four possible stereoisomers.

A mixture of stereoisomers (750 mg) was purified by SFC separation (column: Chiral Pak AD 5 μm, Daicel Chemical Industries, Ltd) and numbered according to the order of elution:

Stereoisomer 1 (First Eluting by SFC): 131 mg $^1$H NMR (CD$_3$OD, 400 MHz): δ 8.45 (s, 1H), 8.19 (d, J=9.6 Hz, 1H), 7.39 (d, J=9.2 Hz, 1H), 4.52~4.57 (m, 1H), 4.04 (s, 4H), 3.97~4.02 (m, 2H), 2.41~2.50 (m, 1H), 1.97~2.04 (m, 1H), 1.32 (d, J=6.4 Hz, 3H).

LC-MS: (m/z) 294.1 (MH+) t$_R$ (minutes, method 1)=1.93 minutes $[α]_D^{20}$=−59.3° (c=0.10, methanol).

Stereoisomer 2 (Second Eluting by SFC): 97 mg $^1$H NMR (CD$_3$OD, 400 MHz): δ 8.43 (s, 1H), 8.25 (d, J=9.2 Hz, 1H), 7.39 (d, J=9.6 Hz, 1H), 5.01~5.06 (m, 1H), 4.09~4.14 (m, 2H), 4.04 (s, 3H), 3.72 (q, J=8.0 Hz, 3H), 2.40~2.46 (m, 1H), 2.10~2.14 (m, 1H), 1.09 (d, J=6.0 Hz, 3H).

LC-MS: (m/z) 294.1 (MH+) t$_R$ (minutes, method 2)=1.73 minutes $[α]_D^{20}$=−28.3° (c=0.10, methanol).

Stereoisomer 3 (Third Eluting by SFC): 37 mg $^1$H NMR (CD$_3$OD variant 400): δ 8.43 (s, 1H), 8.24 (d, J=9.2 Hz, 1H), 7.38 (d, J=9.2 Hz, 1H), 5.00~5.05 (m, 1H), 4.10~4.14 (m, 2H), 4.04 (s, 3H), 3.72 (q, J=8.0 Hz, 3H), 2.41~2.46 (m, 1H), 2.09~2.14 (m, 1H), 1.09 (d, J=6.4 Hz, 3H).

LC-MS: (m/z) 294.1 (MH+) t$_R$ (minutes, method 1)=1.73 minutes

[α]$_D^{20}$=+29.3° (c=0.10, methanol).
Stereoisomer 4 (Fourth Eluting by SFC): 50 mg
$^1$H NMR (H000269489 H20773~029~4A MeOD variant 400): δ 8.46 (s, 1H), 8.20 (d, J=9.2 Hz, 1H), 7.39 (d, J=9.2 Hz, 1H), 4.53~4.57 (m, 1H), 4.04 (s, 3H), 3.97~4.02 (m, 3H), 2.43~2.48 (m, 1H), 1.99~2.04 (m, 1H), 1.32 (d, J=6.4 Hz, 3H).
LC-MS: (m/z) 294.1 (MH+) $t_R$ (minutes, method 1)=1.77 minutes
[α]$_D^{20}$=+62.7° (c=0.10, methanol).

Example 6

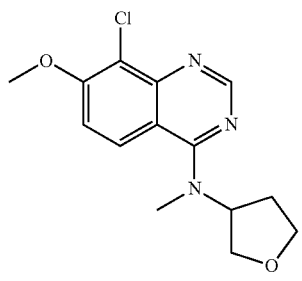 [SMILES: COc1ccc2c(N(C)C3CCOC3)ncnc2c1Cl]

8-Chloro-7-methoxy-N-methyl-N-(tetrahydrofuran-3-yl)quinazolin-4-amine, stereoisomer 1

To an ice-cold solution of stereoisomer 1 of 8-chloro-7-methoxy-N-(tetrahydrofuran-3-yl)quinazolin-4-amine (150 mg, 0.54 mmol) in a mixture of THF (4 mL) and dimethylformamide (2 mL) was added NaH (32 mg, 0.81 mmol, 60% in mineral oil). The mixture was stirred at 0° C. for 30 minutes. Then methyliodide (100 mg, 0.70 mmol) was added at 0° C. The reaction was stirred at room temperature for 3 hours and then quenched with sat. NH$_4$Cl (aq) (2 mL). The crude reaction mixture was concentrated and the residue purified by preparatory TLC (dichloromethane/methanol=50/1) to give 8-chloro-7-methoxy-N-methyl-N-(tetrahydrofuran-3-yl)quinazolin-4-amine (stereoisomer 1).
23 mg (14%)
$^1$H NMR (CD$_3$OD, 400 MHz): δ 8.49 (s, 1H), 8.11 (d, J=9.6 Hz, 1H), 7.39 (d, J=9.6 Hz, 1H), 5.24~5.30 (m, 1H), 4.10~4.13 (m, 1H), 4.06 (s, 3H), 3.94~3.98 (m, 2H), 3.73 (q, J=8.0 Hz, 1H), 3.34 (s, 3H), 2.45~2.49 (m, 1H), 2.13~2.18 (m, 1H).
LC-MS: (m/z) 294.0 (MH+) $t_R$ (minutes, method 3)=2.55 minutes
[α]$_D^{20}$=−19.3° (c=0.10, CHCl$_3$)

8-Chloro-7-methoxy-N-methyl-N-(tetrahydrofuran-3-yl)quinazolin-4-amine, stereoisomer 2

To an ice-cold solution of stereoisomer 2 of 8-chloro-7-methoxy-N-(tetrahydrofuran-3-yl)quinazolin-4-amine (150 mg, 0.54 mmol) in a mixture of THF (4 mL) and DMF (2 mL) was added NaH (32 mg, 0.81 mmol, 60% in mineral oil). The reaction was stirred at 0° C. for 30 minutes Then CH$_3$I (100 mg, 0.70 mmol) was added at 0° C. The reaction was allowed to warm to RT and stirred for 3 hours. The reaction was quenched with sat. NH$_4$Cl (aq) (2 mL). Then concentrated and the residue was purified by preparatory TLC (dichloromethane/methanol=50/1) give stereoisomer 2 of 8-chloro-7-methoxy-N-methyl-N-(tetrahydrofuran-3-yl)quinazolin-4-amine.

25 mg (16%)
$^1$H NMR (H000271637 H20773-033-2B MeOD variant 400): δ 8.49 (s, 1H), 8.11 (d, J=9.6 Hz, 1H), 7.40 (d, J=9.6 Hz, 1H), 5.24-5.31 (m, 1H), 4.10~4.13 (m, 1H), 4.06 (s, 3H), 3.94~3.98 (m, 2H), 3.73 (q, J=7.6 Hz, 1H), 3.34 (s, 3H), 2.44~2.49 (m, 1H), 2.13~2.18 (m, 1H).
LC-MS: (m/z) 294.0 (MH+) $t_R$ (minutes, method 1)=2.11 minutes
[α]$_D^{20}$=−7.7° (c=0.10, CHCl$_3$).

Example 7

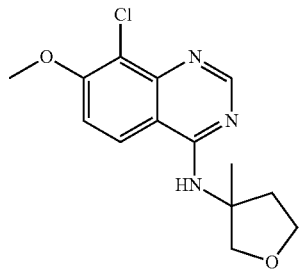 [SMILES: COc1ccc2c(NC3(C)CCOC3)ncnc2c1Cl]

8-Chloro-7-methoxy-N-(3-methyltetrahydrofuran-3-yl)quinazolin-4-amine

To a solution of 4,8-dichloro-7-methoxyquinazoline (350 mg, 1.53 mmol) in DMSO (30 mL) was added 3-methyl-tetrahydrofuran-3-amine (210 mg, 1.53 mmol) and NaHCO$_3$ (257 mg, 3.06 mmol). The mixture was heated at 100° C. for 3 hours. Then cooled to room temperature and quenched with H$_2$O (10 mL). The resulting mixture was extracted with dichloromethane (3×20 ml). The combined organic phases were washed with H$_2$O (50 mL), dried over Na$_2$SO$_4$, filtered, and concentrated. The residue was purified by prep-HPLC to give 8-chloro-7-methoxy-N-(3-methyltetrahydrofuran-3-yl)quinazolin-4-amine 200 mg (45%).

The racemic mixture (200 mg) was purified by SFC (Column: Chiralpak AD 250×30 mm I.D., 5 um) separation and numbered according to the order of elution:
Stereoisomer 1 (First Eluting by SFC): 43 mg
$^1$H NMR (CD$_3$OD, 400 MHz): δ 8.46 (s, 1H), 8.21 (d, J=9.2 Hz, 1H), 7.39 (d, J=9.6 Hz, 1H), 4.19 (d, J=9.2 Hz, 1H), 4.04 (s, 3H), 3.93~3.99 (m, 3H), 2.56~2.62 (m, 1H), 2.13~2.20 (m, 1H), 1.67 (s, 3H).
LC-MS: (m/z) 294.0 (MH+) $t_R$ (minutes, method 4)=2.16 minutes
[α]$_D^{20}$=+8.3° (c=0.10, CHCl$_3$).
Stereoisomer 2 (Second Eluting by SFC): 39 mg
$^1$H NMR (CD$_3$OD, 400): δ 8.46 (s, 1H), 8.21 (d, J=9.2 Hz, 1H), 7.39 (d, J=9.2 Hz, 1H), 4.19 (d, J=9.2 Hz, 1H), 4.04 (s, 3H), 3.93~3.99 (m, 3H), 2.56~2.62 (m, 1H), 2.13~2.20 (m, 1H), 1.67 (s, 3H).
LC-MS: (m/z) 294.0 (MH+) $t_R$ (minutes, method 4)=2.17 minutes
[α]$_D^{20}$=−5.7° (c=0.10, CHCl$_3$).

Example 8

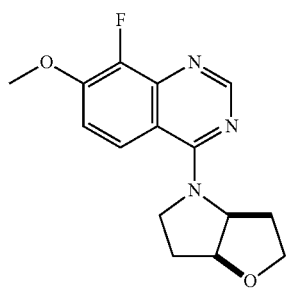

Cis-4-(8-fluoro-7-methoxyquinazolin-4-yl)hexahydro-2H-furo[3,2-b]pyrrole

A mixture of 4-chloro-8-fluoro-7-methoxyquinazoline (320 mg, 1.50 mmol), cis-hexahydro-2H-furo[3,2-b]pyrrole (200 mg, 1.77 mmol) and diisopropylethylamine (457 mg, 3.54 mmol) in DMF (30 mL) was stirred at 100° C. for 12 hrs. The solution was concentrated in vacuo, the residue was diluted with dichloromethane (100 mL), washed with brine (3×10 mL), dried and concentrated in vacuo. The crude product was purified by flash chromatography on silica gel using a gradient of ethyl acetate and petroleum ether to give racemic cis-4-(8-fluoro-7-methoxyquinazolin-4-yl)hexahydro-2H-furo[3,2-b]pyrrole (300 mg, 69%).

The racemate of cis-4-(8-fluoro-7-methoxyquinazolin-4-yl)hexahydro-2H-furo[3,2-b]pyrrole (300 mg) was purified by SFC (Column: IC (250 mm*30 mm, 10 um)) separation and numbered according to the order of elution:

Stereoisomer 1:
100 mg (33%)
$^1$H NMR (CDCl$_3$, 400 MHz): δ 8.62 (s, 1H), 7.90 (dd, J=9.2, 1.6 Hz, 1H), 7.15 (t, J=8.8 Hz, 1H), 5.15 (t, J=4.9 Hz, 1H), 4.60 (d, J=4.2 Hz, 1H), 4.11-4.09 (m, 2H), 4.06 (s, 3H), 3.95-3.91 (m, 2H), 2.44-2.33 (m, 2H), 2.18-2.15 (m, 1H), 2.04-2.01 (m, 1H).
LC-MS (m/z) 290.1 (MH$^+$) t$_R$ (minutes, method 1)=1.81
$[\alpha]_D^{20}$ +181.3° (c=0.10, methanol).

Stereoisomer 2:
100 mg (33%)
$^1$H NMR (CDCl$_3$, 400 MHz): δ 8.63 (s, 1H), 7.91 (dd, J=9.2, 1.6 Hz, 1H), 7.15 (t, J=8.8 Hz, 1H), 5.15 (t, J=4.8 Hz, 1H), 4.60 (t, J=4.4 Hz, 1H), 4.12-4.09 (m, 2H), 4.06 (s, 3H), 3.95-3.91 (m, 2H), 2.44-2.33 (m, 2H), 2.18-2.15 (m, 1H), 2.04-2.01 (m, 1H).
LC-MS (m/z) 290.1 (MH$^+$) t$_R$ (minutes, method 1)=1.80.
$[\alpha]_D^{20}$ −202° (c=0.10, methanol).

Example 9

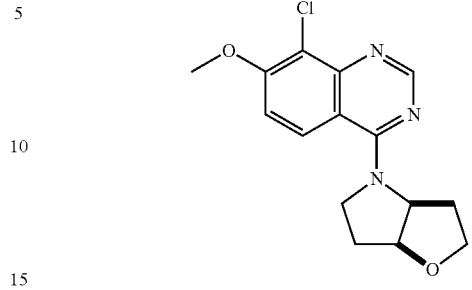

Cis-4-(8-chloro-7-methoxyquinazolin-4-yl)hexahydro-2H-furo[3,2-b]pyrrole

To a solution of 4,8-dichloro-7-methoxyquinazoline (350 mg, 1.53 mmol) in DMF (12 mL) was added hexahydro-2H-furo[3,2-b]pyrrole (208 mg, 1.84 mmol) and diisopropylethylamine (0.54 mL, 3.0 mmol). Nitrogen was bubbled through the mixture for 2 min and it was heated at 100° C. overnight. The reaction was concentrated in vacuo, suspended in ethyl acetate and stirred for 1 hr at room temperature. The solid was filtered off and washed with ethyl acetate to give 4-(8-chloro-7-methoxyquinazolin-4-yl)hexahydro-2H-furo[3,2-b]pyrrole (400 mg, 99%). The racemate of 4-(8-chloro-7-methoxyquinazolin-4-yl)hexahydro-2H-furo[3,2-b]pyrrole (400 mg) was purified by SFC (Column: Chiral Cel OJ 20 μm, Daicel Chemical Industries, Ltd 250×30 mm I.D) separation and numbered according to the order of elution:

Stereoisomer 1
106 mg, (26.5%)
$^1$H NMR (CD$_3$OD, 400 MHz): δ 8.47 (s, 1H), 8.31 (d, J=9.2 Hz, 1H), 7.40 (d, J=9.6 Hz, 1H), 5.20 (t, J=4.8 Hz, 1H), 4.61 (t, J=4.0 Hz, 1H), 4.14~4.18 (m, 2H), 4.08 (s, 3H), 3.92~3.95 (m, 2H), 2.43~2.48 (m, 1H), 2.29~2.32 (m, 1H), 2.07~2.13 (m, 1H).
LC-MS (m/z) 306.1 (MH$^+$) t$_R$ (minutes, method 1)=1.88
$[\alpha]_D^{20}$ +280° (c=0.10, methanol).

Stereoisomer 2:
102 mg (25.5%)
$^1$H NMR (CD$_3$OD, 400 MHz): δ 8.44 (s, 1H), 8.28 (d, J=9.6 Hz, 1H), 7.37 (d, J=9.6 Hz, 1H), 5.17 (t, J=4.8 Hz, 1H), 4.59 (t, J=4.0 Hz, 1H), 4.09~4.15 (m, 2H), 4.05 (s, 3H), 3.87~3.94 (m, 2H), 2.37~2.48 (m, 1H), 2.24~2.32 (m, 1H), 1.99~2.15 (m, 1H).
LC-MS (m/z) 306.1 (MH$^+$) t$_R$ (minutes, method 1)=1.89
$[\alpha]_D^{20}$ −301° (c=0.10, methanol).

Intermediate III

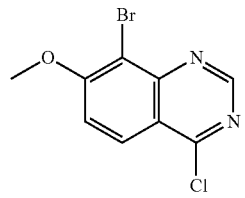

8-Bromo-4-chloro-7-methoxyquinazoline

Step 1:

To a suspension of 2-amino-3-bromo-4-methoxybenzoic acid (CAS1180497-47-5) (5.50 g, 22.4 mmol) in trimethoxymethane (100 mL) was added NH₄OAc (17.2 g, 224 mmol). The mixture was heated at 90° C. for 12 hrs. The mixture was cooled to 25° C., the solid was filtered off, washed with H₂O (50 mL) and dried in vacuo to give 8-bromo-7-methoxyquinazolin-4(3H)-one 3.50 g (61.4%).

Step 2:

To an ice-cold solution of 8-bromo-7-methoxyquinazolin-4(3H)-one (3.50 g, 13.7 mmol) in dry toluene (50 mL) was added diisopropylethylamine (7.09 g, 54.9 mmol) and POCl₃ (18 g, 0.12 mol) dropwise. The mixture was heated at 100° C. for 12 hrs, then cooled to 25° C. and poured into H₂O (100 mL). The aqueous layer was extracted with dichloromethane (100 mL). The organic layer was dried over Na₂SO₄, filtered and concentrated in vacuo. The crude product was purified by flash chromatography on silica gel using a gradient of dichloromethane and ethyl acetate to give 8-bromo-4-chloro-7-methoxyquinazoline 2.4 g, (64%).

Example 10

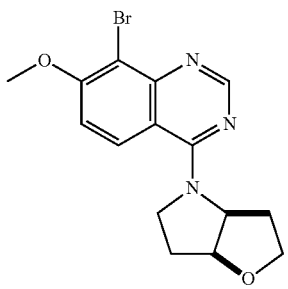

Cis-4-(8-bromo-7-methoxyquinazolin-4-yl)hexahydro-2H-furo[3,2-b]pyrrole

To a solution of 8-bromo-4-chloro-7-methoxyquinazoline (1.30 g, 4.75 mmol) in dry dimethylformamide (20 mL) was added hexahydro-2H-furo[3,2-b]pyrrole (860 mg, 7.60 mmol) and diisopropylethylamine (1.84 g, 14.3 mmol). Nitrogen was bubbled through the mixture for 5 min and it was heated at 100° C. for 12 hrs under N₂. The mixture was concentrated in vacuo, the residue was dissolved in dichloromethane (50 mL). The mixture was adjusted to pH 8 by sat. aq. NaHCO₃. The aqueous layer was extracted with dichloromethane (50 mL). The combined organic phases were dried over Na₂SO₄, filtered and concentrated. The crude product was purified by chromatography on silica gel using a gradient of dichloromethane and ethyl acetate to give 4-(8-bromo-7-methoxyquinazolin-4-yl)hexahydro-2H-furo[3,2-b]pyrrole 1.6 g (95%).

The racemate of cis-4-(8-bromo-7-methoxyquinazolin-4-yl)hexahydro-2H-furo[3,2-b]pyrrole (1.6 g) was purified by SFC (Column: AD 250 mm*50 mm, 10 um) separation and numbered according to the order of elution:

Stereoisomer 1:

651 mg (39.3%)

¹H NMR (CDCl₃, 400 MHz): δ 8.70 (s, 1H), 8.11 (d, J=9.2 Hz, 1H), 7.12 (d, J=9.2 Hz, 1H), 5.16-5.14 (m, 1H), 4.58-4.55 (m, 1H), 4.14-4.08 (m, 2H), 4.05 (s, 3H), 3.94-3.91 (m, 2H), 2.44-2.31 (m, 2H), 2.16-2.15 (m, 1H), 2.03-1.95 (m, 1H).

LC-MS (m/z) 350.0 (MH⁺) $t_R$ (minutes, method 1)=2.02

$[\alpha]_D^{20}$ +303° (c=0.10, CHCl₃)

Stereoisomer 2:

564 mg (35.2%)

¹H NMR (CDCl₃, 400 MHz): δ 8.70 (s, 1H), 8.11 (d, J=9.2 Hz, 1H), 7.12 (d, J=9.2 Hz, 1H), 5.16-5.14 (m, 1H), 4.58-4.56 (m, 1H), 4.13-4.07 (m, 2H), 4.05 (s, 3H), 3.94-3.90 (m, 2H), 2.44-2.31 (m, 2H), 2.16-2.14 (m, 1H), 2.01-1.98 (m, 1H).

LC-MS (m/z) 350.0 (MH⁺) $t_R$ (minutes, method 1)=2.02

$[\alpha]_D^{20}$ −233° (c=0.10, CHCl₃)

Example 11

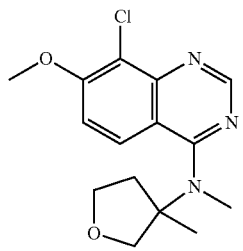

8-Chloro-7-methoxy-N-methyl-N-(3-methyltetrahydrofuran-3-yl)quinazolin-4-amine

Stereoisomer 1

To an ice-cold solution of stereoisomer 2 of (example 7) 8-chloro-7-methoxy-N-(3-methyltetrahydrofuran-3-yl)quinazolin-4-amine (200 mg, 0.681 mmol) in THF (10 mL) was added NaH (60% dispersion in mineral oil) (41 mg, 1.0 mmol). The mixture was stirred at 0° C. for 30 min. Then MeI (126 mg, 0.885 mmol) was added at 0° C. and it was stirred at 25° C. for 3 hrs. H₂O (5 mL) was added to the mixture and the THF was removed in vacuo. The residue was extracted with dichloromethane (2×20 mL). The combined organic phases were washed with H₂O (10 mL), dried over Na₂SO₄, filtered, and concentrated in vacuo. The crude product was purified by preparative TLC, eluting with dichloromethane/methanol=50/1, to give stereoisomer of 8-chloro-7-methoxy-N-methyl-N-(3-methyltetrahydrofuran-3-yl)quinazolin-4-amine 156 mg (70.7%).

¹H NMR (CD₃OD, 400 MHz): δ 8.49 (s, 1H), 8.08 (d, J=9.2 Hz, 1H), 7.39 (d, J=9.6 Hz, 1H), 4.37 (d, J=8.8 Hz, 1H), 4.05 (s, 3H), 3.97-3.85 (m, 3H), 3.35 (s, 3H), 2.47-2.41 (m, 1H), 2.31-2.27 (m, 1H), 1.69 (s, 3H).

LC-MS (m/z) 308.1 (MH⁺) $t_R$ (minutes, method 1)=1.932

$[\alpha]_D^{20}$ +20.33° (c=0.10, methanol).

Stereoisomer 2

To an ice-cold solution of stereoisomer 1 of (example 7) 8-chloro-7-methoxy-N-(3-methyltetrahydrofuran-3-yl)quinazolin-4-amine (200 mg, 0.681 mmol) in THF (10 mL) was added NaH (60% dispersion in mineral oil) (41 mg, 1.0 mmol). The mixture was stirred at 0° C. for 30 min and then MeI (126 mg, 0.885 mmol) was added. The mixture was heated to 25° C. and stirred for 3 hrs. To the reaction mixture was added H₂O (5 mL) and THF was removed in vacuo. The residue was extracted with dichloromethane (2×20 mL). The combined organic phases were washed with water (10 mL), dried over Na$_2$SO$_4$ and concentrated in vacuo. The crude product was purified by preparative TLC, eluting with dichloromethane/methanol=50/1, to give stereoisomer 2 of 8-chloro-7-methoxy-N-methyl-N-(3-methyltetrahydrofuran-3-yl)quinazolin-4-amine 141 mg (63.9%).

$^1$H NMR (CD$_3$OD, 400 MHz): δ 8.49 (s, 1H), 8.08 (d, J=9.2 Hz, 1H), 7.39 (d, J=9.6 Hz, 1H), 4.37 (d, J=8.8 Hz, 1H), 4.05 (s, 3H), 3.97-3.85 (m, 3H), 3.35 (s, 3H), 2.47-2.44 (m, 1H), 2.31-2.6 (m, 1H), 1.68 (s, 3H).

LC-MS (m/z) 308.1 (MH$^+$) t$_R$ (minutes, method 1)=1.950 [α]$_D^{20}$ −26.33° (c=0.10, methanol).

Example 12

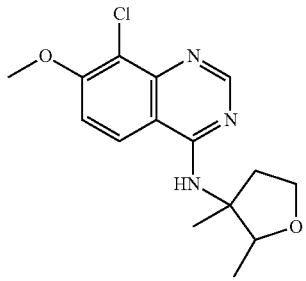 [SMILES: COc1ccc2c(NC3(C)CCOC3C)ncnc2c1Cl]

8-Chloro-N-(2,3-dimethyltetrahydrofuran-3-yl)-7-methoxyquinazolin-4-amine

To a solution of 4,8-dichloro-7-methoxyquinazoline (1.8 g, 7.9 mmol) in DMSO (30 mL) was added 2,3-dimethyl-tetrahydrofuran-3-amine (905 mg, 7.86 mmol) and NaHCO$_3$ (660 mg, 7.86 mmol). The mixture was heated at 100° C. for 3 hrs and then cooled to 20° C. H$_2$O (30 mL) was added to the mixture, the precipitate was filtered off and washed with water (50 mL), dried and purified by flash chromatography on silica gel using a gradient of dichloromethane and methanol to give 8-chloro-N-(2,3-dimethyltetrahydrofuran-3-yl)-7-methoxyquinazolin-4-amine (1.2 g, 50

The mixture of all 4 stereoisomers of 8-chloro-N-(2,3-dimethyltetrahydrofuran-3-yl)-7-methoxyquinazolin-4-amine 2.4 g was purified by SFC (Column: AS 300 mm*50 mm, 10 um). The stereoisomers were numbered according to their order of elution.

Stereoisomer 1:
400 mg (15.8%)
$^1$H NMR (CD$_3$OD, 400 MHz): δ 8.47 (s, 1H), 8.17 (d, J=9.2 Hz, 1H), 7.38 (d, J=8.8 Hz, 1H), 4.52 (q, J=6.4 Hz, 1H), 4.04 (s, 3H), 4.02-3.96 (m, 1H), 3.86 (q, J=8.4 Hz, 1H), 2.61-2.55 (m, 1H), 2.19-2.13 (m, 1H), 1.65 (s, 3H), 1.06 (d, J=6.4 Hz, 3H).

LC-MS (m/z) 308.1 (MH$^+$) t$_R$ (minutes, method 5)=1.267 [α]$_D^{20}$+20.00° (c=0.10, methanol).

Stereoisomer 2:
300 mg (11.9%)
$^1$H NMR (CD$_3$OD, 400 MHz): δ 8.47 (s, 1H), 8.16 (d, J=9.2 Hz, 1H), 7.38 (d, J=9.6 Hz, 1H), 4.51 (q, J=6.4 Hz, 1H), 4.04 (s, 3H), 4.02-3.97 (m, 1H), 3.86 (q, J=8.4 Hz, 1H), 2.61-2.55 (m, 1H), 2.19-2.13 (m, 1H), 1.65 (s, 3H), 1.06 (d, J=6.4 Hz, 3H).

LC-MS (m/z) 308.1 (MH$^+$) t$_R$ (minutes, method 5)=1.272 [α]$_D^{20}$ −13.33° (c=0.10, methanol).

Stereoisomer 3:
600 mg (23.7%)
$^1$H NMR (CD$_3$OD, 400 MHz): δ 8.46 (s, 1H), 8.20 (d, J=9.2 Hz, 1H), 7.36 (d, J=9.2 Hz, 1H), 4.47 (q, J=6.4 Hz, 1H), 4.03 (s, 3H), 3.99-3.90 (m, 2H), 2.71-2.66 (m, 1H), 2.26-2.21 (m, 1H), 1.57 (s, 3H), 1.26 (d, J=6.4 Hz, 3H).

LC-MS (m/z) 308.1 (MH$^+$) t$_R$ (minutes, method 5)=1.295 [α]$_D^{20}$ −25.33° (c=0.10, methanol).

Stereoisomer 4:
700 mg (27.7%)
$^1$H NMR (CD$_3$OD, 400 MHz): δ 8.46 (s, 1H), 8.21 (d, J=9.2 Hz, 1H), 7.36 (d, J=9.2 Hz, 1H), 4.47 (q, J=6.4 Hz, 1H), 4.04 (s, 3H), 3.99-3.90 (m, 2H), 2.71-2.66 (m, 1H), 2.26-2.21 (m, 1H), 1.57 (s, 3H), 1.26 (d, J=6.4 Hz, 3H).

LC-MS (m/z) 308.1 (MH$^+$) t$_R$ (minutes, method 5)=1.30 [α]$_D^{20}$+43.67° (c=0.10, methanol).

Example 13

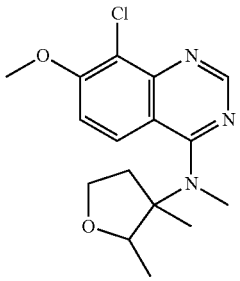

8-Chloro-N-(2,3-dimethyltetrahydrofuran-3-yl)-7-methoxy-N-methylquinazolin-4-amine Stereoisomer 1:
To an ice-cold solution of stereoisomer 1 example 12 (200 mg, 0.650 mmol) in THF (10 mL) was added NaH (60% dispersion in mineral oil) (39 mg, 0.98 mmol). The mixture was stirred at 0° C. for 30 min and then MeI (120 mg, 0.845 mmol) was added. The reaction was allowed to warm to 25° C. and stirred for 3 hrs. H$_2$O (5 mL) was added to the mixture and the THF was removed in vacuo. The residue was extracted with dichloromethane (2×20 mL). The combined organic phases were washed with H$_2$O (10 mL), dried over Na$_2$SO$_4$, concentrated in vacuo and purified by preparative TLC, using dichloromethane/methanol=50/1, to give stereoisomer 1 of 8-chloro-N-(2,3-dimethyltetrahydrofuran-3-yl)-7-methoxy-N-methylquinazolin-4-amine (118 mg, 57%).

$^1$H NMR (CD$_3$OD, 400 MHz): δ 8.54 (s, 1H), 8.12 (d, J=9.2 Hz, 1H), 7.46 (d, J=9.2 Hz, 1H), 4.09 (s, 3H), 4.07-4.04 (m, 1H), 3.94-3.88 (m, 1H), 3.40 (s, 3H), 2.66-2.58 (m, 1H), 2.26-2.21 (m, 1H), 1.73 (s, 3H), 0.96 (d, J=6.4 Hz, 3H).

LC-MS (m/z) 322.2 (MH$^+$) t$_R$ (minutes, method 5)=1.46 [α]$_D^{20}$ −9.67° (c=0.10, methanol).

Stereoisomer 2:
To an ice-cold solution of stereoisomer 2 example (200 mg, 0.650 mmol) in THF (10 mL) was added NaH (60% dispersion in mineral oil) (39 mg, 0.98 mmol). The mixture was stirred at 0° C. for 30 min and then MeI (120 mg, 0.845 mmol) was added. The reaction was stirred at 25° C. for 3 hrs and then H$_2$O (5 mL) was added. THF was removed in vacuo and the residue extracted with dichloromethane (2×20 mL). The combined organic phases were washed with H₂O (10 mL), dried over Na₂SO₄, and concentrated in vacuo. The crude product was purified by preparative TLC, using dichloromethane/methanol=50/1, to give stereoisomer 2 of 8-chloro-N-(2,3-dimethyltetrahydrofuran-3-yl)-7-methoxy-N-methylquinazolin-4-amine (120 mg, 57%).

¹H NMR (CD₃OD, 400 MHz): δ 8.54 (s, 1H), 8.12 (d, J=9.2 Hz, 1H), 7.46 (d, J=9.2 Hz, 1H), 4.09 (s, 3H), 4.07-4.04 (m, 1H), 3.94-3.88 (m, 1H), 3.40 (s, 3H), 2.66-2.58 (m, 1H), 2.25-2.21 (m, 1H), 1.73 (s, 3H), 0.96 (d, J=6.0 Hz, 3H).

LC-MS (m/z) 322.2 (MH⁺) $t_R$ (minutes, method 5)=1.46

$[α]_D^{20}$+5.33° (c=0.10, methanol).

Stereoisomer 3:

To an ice-cold solution of stereoisomer 3 example 12 (200 mg, 0.650 mmol) in THF (10 mL) was added NaH (60% dispersion in mineral oil) (39 mg, 0.98 mmol). The mixture was stirred at 0° C. for 30 min and then MeI (120 mg, 0.845 mmol) was added at 0° C. The reaction was stirred at 25° C. for 3 hrs and then H₂O (5 mL) was added. THF was removed in vacuo and the residue was extracted with dichloromethane (2×20 mL). The combined organic phases were washed with H₂O (10 mL), dried over Na₂SO₄ and concentrated in vacuo. The crude product was purified by preparative TLC, using dichloromethane/methanol=50/1, to give stereoisomer 3 of 8-chloro-N-(2,3-dimethyltetrahydrofuran-3-yl)-7-methoxy-N-methylquinazolin-4-amine (78 mg, 37%).

¹H NMR (CD₃OD, 400 MHz): δ 8.61 (s, 1H), 8.08 (d, J=9.6 Hz, 1H), 7.48 (d, J=9.6 Hz, 1H), 4.50-4.47 (m, 1H) 4.10 (s, 3H), 3.95-3.91 (m, 1H), 3.88-3.84 (m, 1H), 3.31 (s, 3H), 2.67-2.62 (m, 1H), 2.32-2.26 (m, 1H), 1.65 (s, 3H), 1.39 (d, J=6.4 Hz, 3H).

LC-MS (m/z) 322.2 (MH⁺) $t_R$ (minutes, method 5)=1.50

$[α]_D^{20}$ −49.33° (c=0.10, methanol).

Stereoisomer 4:

To an ice-cold solution of stereoisomer 4 example 12 (200 mg, 0.650 mmol) in THF (10 mL) was added NaH (60% dispersion in oil) (39 mg, 0.98 mmol). The mixture was stirred at 0° C. for 30 min and then MeI (120 mg, 0.845 mmol) was added. The reaction was stirred at 25° C. for 3 hrs. Then H₂O (5 mL) was added and THF was removed in vacuo. The residue was extracted with dichloromethane (2×20 mL). The combined organic phases were washed with H₂O (10 mL), dried over Na₂SO₄, and concentrated in vacuo. The crude product was purified by preparative TLC, using dichloromethane/methanol=50/1, to give stereoisomer 4 of 8-chloro-N-(2,3-dimethyltetrahydrofuran-3-yl)-7-methoxy-N-methylquinazolin-4-amine (92 mg, 44%).

¹H NMR (CD₃OD, 400 MHz): δ 8.62 (s, 1H), 8.08 (d, J=9.6 Hz, 1H), 7.48 (d, J=9.6 Hz, 1H), 4.50-4.47 (m, 1H) 4.10 (s, 3H), 3.95-3.91 (m, 1H), 3.88-3.84 (m, 1H), 3.32 (s, 3H), 2.67-2.62 (m, 1H), 2.32-2.26 (m, 1H), 1.65 (s, 3H), 1.39 (d, J=7.6 Hz, 3H).

LC-MS (m/z) 322.2 (MH⁺) $t_R$ (minutes, method 5)=1.50

$[α]_D^{20}$+33.33° (c=0.10, methanol).

Example 14

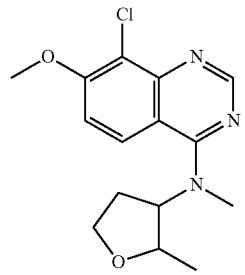

8-Chloro-7-methoxy-N-methyl-N-(2-methyltetrahydrofuran-3-yl)quinazolin-4-amine

Stereoisomer 1:

To an ice-cold solution of stereoisomer 1 of example 5 (8-chloro-7-methoxy-N-(2-methyltetrahydrofuran-3-yl)quinazolin-4-amine) (250 mg, 0.851 mmol) in THF (10 mL) was added a 60% suspension of NaH in mineral oil (61 mg, 1.5 mmol). The mixture was stirred at 0° C. for 30 min and then MeI (181 mg, 1.28 mmol) was added at 0° C. After stirring at 30° C. for 3 hrs H₂O (5 mL) was added to the mixture. THF was removed in vacuo and the residue was extracted with dichloromethane (2×20 mL). The combined organic phases were washed with H₂O (10 mL), dried over Na₂SO₄ and concentrated in vacuo. The crude product was purified by preparative TLC, using dichloromethane/methanol=50/1, to give stereoisomer 1 of 8-chloro-7-methoxy-N-methyl-N-2-methyltetrahydrofuran-3-yl)quinazolin-4-amine (192 mg, 70.

¹H NMR (CDCl₃, 400 MHz): δ 8.75 (s, 1H), 7.92 (d, J=8.8 Hz, 1H), 7.17 (d, J=9.6 Hz, 1H), 4.82-4.76 (m, 1H), 4.18 (q, J=6.4 Hz, 1H), 4.08 (s, 3H), 4.05-4.02 (m, 2H), 3.29 (s, 3H), 2.54-2.49 (m, 1H), 2.18-2.11 (m, 1H), 1.28 (d, J=6.0 Hz, 3H).

LC-MS (m/z) 308.1 (MH⁺) $t_R$ (minutes, method 1)=1.96

$[α]_D^{20}$ −46.00° (c=0.10, methanol).

Stereoisomer 2:

To an ice-cold solution of stereoisomer 2 of example 5 (8-chloro-7-methoxy-N-(2-methyltetrahydrofuran-3-yl)quinazolin-4-amine) (250 mg, 0.851 mmol) in THF (10 mL) was added a 60% suspension in mineral oil of NaH (61 mg, 1.5 mmol). The mixture was stirred at 0° C. for 30 min and then MeI (181 mg, 1.28 mmol) was added. The reaction was stirred at 30° C. for 3 hrs before addition of H₂O (5 mL). THF was removed in vacuo and the residue was extracted with dichloromethane (2×20 mL). The combined organic phases were washed with H₂O (10 mL), dried over Na₂SO₄, and concentrated in vacuo. The crude product was purified by preparative TLC, using dichloromethane/methanol=50/1, to give stereoisomer 2 of 8-chloro-7-methoxy-N-methyl-N-(-2-methyltetrahydrofuran-3-yl)quinazolin-4-amine (217 mg, 80%).

¹H NMR (CDCl₃, 400 MHz): δ 8.70 (s, 1H), 7.95 (d, J=9.6 Hz, 1H), 7.14 (d, J=9.6 Hz, 1H), 5.47-5.42 (m, 1H), 4.20-4.17 (m, 1H), 4.07 (s, 3H), 4.05-4.02 (m, 2H), 3.73 (q,

J=8.8 Hz, 1H), 3.38 (s, 3H), 2.47-2.42 (m, 1H), 2.33-2.30 (m, 1H), 1.28 (d, J=6.4 Hz, 3H).

LC-MS (m/z) 308.1 (MH$^+$) $t_R$ (minutes, method 1)=1.94 $[\alpha]_D^{20}$ −48.00° (c=0.10, methanol).

Stereoisomer 3:

To an ice-cold solution of stereoisomer 3 of example 5 (8-chloro-7-methoxy-N-(2-methyltetrahydrofuran-3-yl)quinazolin-4-amine) (160 mg, 0.545 mmol) in THF (10 mL) was added a 60% suspension of NaH in mineral oil (39 mg, 0.98.mmol) and the mixture was stirred at 0° C. for 30 min. MeI (116 mg, 0.817 mmmol) was added at 0° C. The reaction was stirred at 30° C. for 3 hrs and then H$_2$O (5 mL) was added. THF was removed in vacuo and the residue was extracted with dichloromethane (2×20 mL). The combined organic phases were washed with H$_2$O (10 mL), dried over Na$_2$SO$_4$, and concentrated in vacuo. The crude product was purified by preparative TLC, using dichloromethane/methanol=50/1) to give stereoisomer 3 of 8-chloro-7-methoxy-N-methyl-N-(-2-methyltetrahydrofuran-3-yl)quinazolin-4-amine 139 mg (81%).

$^1$H NMR (CDCl$_3$, 400 MHz): δ 8.70 (s, 1H), 7.95 (d, J=9.6 Hz, 1H), 7.14 (d, J=9.2 Hz, 1H), 5.47-5.42 (m, 1H), 4.20-4.16 (m, 1H), 4.07 (s, 3H), 4.05-4.02 (m, 2H), 3.75-3.73 (m, 1H), 3.38 (s, 3H), 2.47-2.42 (m, 1H), 2.34-2.30 (m, 1H), 1.28 (d, J=6.0 Hz, 3H).

LC-MS (m/z) 308.1 (MH$^+$) $t_R$ (minutes, method 1)=1.96 $[\alpha]_D^{20}$+52.67° (c=0.10, methanol).

Stereoisomer 4:

To an ice-cold solution of stereoisomer 4 of example 5 (8-chloro-7-methoxy-N-(2-methyltetrahydrofuran-3-yl)quinazolin-4-amine) (200 mg, 0.681 mmol) in THF (10 mL) was added a 60% suspension of NaH in mineral oil (49 mg, 1.2 mmol). The mixture was stirred at 0° C. for 30 min and then MeI (145 mg, 1.02 mmol) was added. The reaction was stirred at 30° C. for 3 hrs and then H$_2$O (5 mL) was added. THF was removed in vacuo and the residue was extracted with dichloromethane (2×20 mL). The combined organic phases were washed with H$_2$O (10 mL), dried over Na$_2$SO$_4$, and concentrated in vacuo. The crude product was purified by preparative TLC, dichloromethane/methanol=50/1, to give stereoisomer 4 of 8-chloro-7-methoxy-N-methyl-N-(2-methyltetrahydrofuran-3-yl)quinazolin-4-amine 184 mg (85%).

$^1$H NMR (CDCl$_3$, 400 MHz): δ 8.75 (s, 1H), 7.92 (d, J=9.2 Hz, 1H), 7.17 (d, J=9.2 Hz, 1H), 4.82-4.76 (m, 1H), 4.19-4.16 (m, 1H), 4.08 (s, 3H), 4.05-4.02 (m, 2H), 3.29 (s, 3H), 2.54-2.49 (m, 1H), 2.18-2.11 (m, 1H), 1.28 (d, J=6.4 Hz, 3H).

LC-MS (m/z) 308.1 (MH$^+$) $t_R$ (minutes, method 1)=1.94 $[\alpha]_D^{20}$+35.33° (c=0.10, methanol).

Example 15

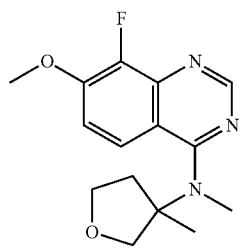

8-Fluoro-7-methoxy-N-methyl-N-(3-methyltetrahydrofuran-3-yl)quinazolin-4-amine

Stereoisomer 1:

To solution of stereoisomer 1 of example 1 (8-fluoro-7-methoxy-N-(3-methyltetrahydrofuran-3-yl)quinazolin-4-amine) (200 mg, 0.721 mmol) in THF (4 mL) was added a 60% suspension of NaH in mineral oil (43 mg, 1.1 mmol) at 0° C. After stirring for 30 min the reaction was heated to 20° C. MeI (154 mg, 1.08 mmol) was added and the reaction was stirred for 12 hrs. The reaction was quenched with sat. aq. NH$_4$Cl (0.5 mL) and concentrated in vacuo. The residue was diluted with dichloromethane (20 mL), washed with brine (10 mL), dried, and concentrated in vacuo. The crude product was purified by preparative TLC, using ethyl acetate, to give stereoisomer 1 of 8-fluoro-7-methoxy-N-methyl-N-(3-methyltetrahydrofuran-3-yl)quinazolin-4-amine 150 mg (70%).

$^1$H NMR (CDCl$_3$, 400 MHz): δ 8.65 (s, 1H), 7.73 (dd, J=9.6, 2.0 Hz, 1H), 7.19 (dd, J=9.6, 8.0 Hz, 1H), 4.35 (d, J=8.8 Hz, 1H), 4.07 (s, 3H), 4.02-3.88 (m, 3H), 3.31 (s, 3H), 2.41-2.35 (m, 1H), 2.28-2.24 (m, 1H), 1.71 (s, 3H).

LC-MS (m/z) 292.1 (MH$^+$) $t_R$ (minutes, method 1)=1.83 $[\alpha]_D^{20}$+38.33° (c=0.10, methanol).

Stereoisomer 2:

To a solution of stereoisomer 2 of example 1 (8-fluoro-7-methoxy-N-(3-methyltetrahydrofuran-3-yl)quinazolin-4-amine) (200 mg, 0.721 mmol) in THF (4 mL) was added a 60% suspension in mineral oil NaH (43 mg, 1.1 mmol) at 0° C. and the reaction was stirred for 30 min before being heated at 20° C. MeI (154 mg, 1.08 mmol) was added and stirring continued for 12 hrs. The solution was quenched with sat. aq. NH$_4$Cl (1 mL) and concentrated in vacuo. The residue was diluted with dichloromethane (20 mL), washed with brine (3×8 mL), dried over MgSO$_4$ and concentrated in vacuo. The crude product was purified by preparative TLC, using ethyl acetate, to give stereoisomer 2 of 8-fluoro-7-methoxy-N-methyl-N-(3-methyltetrahydrofuran-3-yl)quinazolin-4-amine 160 mg (75%).

$^1$H NMR (CDCl$_3$, 400 MHz): δ 8.65 (s, 1H), 7.73 (dd, J=9.6, 1.6 Hz, 1H), 7.18 (dd, J=9.2, 8.0 Hz, 1H), 4.35 (d, J=9.2 Hz, 1H), 4.02 (s, 3H), 4.00-3.88 (m, 3H), 3.31 (s, 3H), 2.43-2.35 (m, 1H), 2.28-2.24 (m, 1H), 1.71 (s, 3H).

LC-MS (m/z) 292.1 (MH$^+$) $t_R$ (minutes, method 1)=1.83 $[\alpha]_D^{20}$ −30.00° (c=0.10, methanol).

Example 16

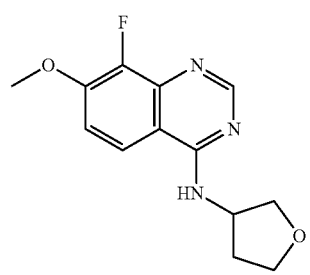 [SMILES: COc1ccc2c(NC3CCOC3)ncnc2c1F]

8-Fluoro-7-methoxy-N-(tetrahydrofuran-3-yl)quinazolin-4-amine

A solution of 4-chloro-8-fluoro-7-methoxyquinazoline (400 mg, 1.88 mmol) tetrahydrofuran-3-amine (192 mg, 2.26 mmol) and diisopropylethylamine (486 mg, 3.76 mmol) in DMF (10 mL) was stirred at 100° C. for 3 hrs. The reaction mixture was concentrated in vacuo and purified by flash chromatography on silica gel using a gradient dichloromethane/ethyl acetate to give 8-fluoro-7-methoxy-N-(tetrahydrofuran-3-yl)quinazolin-4-amine 360 mg (72%).

The racemate of 8-fluoro-7-methoxy-N-(tetrahydrofuran-3-yl)quinazolin-4-amine (360 mg) was purified by SFC (Column: AD-H (250 mm*30 mm, 5 um)) separation and numbered according to the order of elution:

Stereoisomer 1:
150 mg (42%)
$^1$H NMR (CDCl$_3$, 400 MHz): δ 8.66 (s, 1H), 7.48 (dd, J=9.2, 1.6 Hz, 1H), 7.22-7.18 (m, 1H), 5.86 (d, J=6.4 Hz, 1H), 4.99-4.94 (m, 1H), 4.05-3.99 (m, 1H), 3.99 (s, 3H), 3.97-3.96 (m, 1H), 3.91-3.86 (m, 2H), 2.49-2.43 (m, 1H), 2.05-2.00 (m, 2H).
LC-MS (m/z) 264.1 (MH$^+$) $t_R$ (minutes, method 1)=1.72
$[\alpha]_D^{20}$ +29.33° (c=0.10, methanol).

Stereoisomer 2:
150 mg (42%)
$^1$H NMR (CDCl$_3$, 400 MHz): δ 8.66 (s, 1H), 7.48 (d, J=8.8 Hz, 1H), 7.22-7.18 (m, 1H), 5.86 (d, J=6.4 Hz, 1H), 4.99-4.94 (m, 1H), 4.05-4.00 (m, 1H), 4.00 (s, 3H), 3.97-3.96 (m, 1H), 3.91-3.88 (m, 2H), 2.49-2.44 (m, 1H), 2.05-2.00 (m, 2H).
LC-MS (m/z) 264.1 (MH$^+$) $t_R$ (minutes, method 1)=1.72
$[\alpha]D^{20}$ −34.67° (c=0.10, methanol).

Example 17

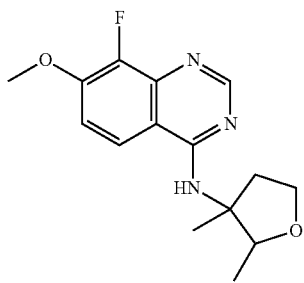 [SMILES: COc1ccc2c(NC3(C)CCOC3C)ncnc2c1F]

N-(2,3-Dimethyltetrahydrofuran-3-yl)-8-fluoro-7-methoxyquinazolin-4-amine

To a solution of 4-chloro-8-fluoro-7-methoxyquinazoline (1.00 g, 4.70 mmol) in DMSO (15 mL) was added 2,3-dimethyltetrahydrofuran-3-amine (541 mg, 4.70 mmol) and NaHCO$_3$ (395 mg, 4.70 mmol). The mixture was heated at 100° C. for 3 hrs and then cooled to 25° C. H$_2$O (50 mL) was added and the mixture was extracted with dichloromethane (2×50 mL). The combined organic phases were washed with water (2×50 mL), dried over Na$_2$SO$_4$, and concentrated in vacuo. The crude product was purified by flash chromatography on silica gel using a gradient of dichloromethane and methanol, to give N-(2,3-dimethyltetrahydrofuran-3-yl)-8-fluoro-7-methoxyquinazolin-4-amine 700 mg (51%).

The mixture of all 4 stereoisomers of N-(2,3-dimethyltetrahydrofuran-3-yl)-8-fluoro-7-methoxyquinazolin-4-amine 2.3 g was purified by SFC (Column: Chiral Pak AD, 5 μm, Daicel Chemical Industries, Ltd 250×30 mm I.D).

Stereoisomer 3:
300 mg (13%)
$^1$H NMR (CDCl3, 400 MHz): δ 8.66 (s, 1H), 7.43-7.41 (m, 1H), 7.21-7.17 (m, 1H), 5.74 (s, 1H), 4.05 (s, 3H), 3.92-3.85 (m, 3H), 2.97-2.91 (m, 1H), 2.10-2.03 (m, 1H), 1.71 (s, 3H), 1.36 (d, J=6.4 Hz, 3H).
LC-MS (m/z) 292.1 (MH$^+$) $t_R$ (minutes, method 1)=1.88
$[\alpha]_D^{20}$ −25.67° (c=0.10, methanol).

Stereoisomer 4:
300 mg (13%)
$^1$H NMR (CDCl3, 400 MHz): δ 8.64 (s, 1H), 7.42-7.39 (m, 1H), 7.19-7.15 (m, 1H), 5.71 (s, 1H), 4.02 (s, 3H), 3.89-3.82 (m, 3H), 2.94-2.88 (m, 1H), 2.08-2.01 (m, 1H), 1.69 (s, 3H), 1.33 (d, J=6.4 Hz, 3H).
LC-MS (m/z) 292.1 (MH$^+$) $t_R$ (minutes, method 1)=1.86
$[\alpha]_D^{20}$ +27.33° (c=0.10, methanol)

From the first SFC purification a mixture of stereoisomer 1 and 2 was obtained. This mixture was subjected to a second purification by SFC(Column: Chiral Pak AS, 5 μm, Daicel Chemical Industries, Ltd 250×30 mm I.D.) chromatography to yield:

Stereoisomer 2
600 mg (26%)
$^1$H NMR (CDCl$_3$, 400 MHz): δ 8.60 (s, 1H), 7.45-7.42 (m, 1H), 7.15-7.11 (m, 1H), 5.63 (s, 1H), 4.27 (q, J=6.4 Hz, 1H), 3.99 (s, 3H), 3.95-3.85 (m, 2H), 2.72-2.66 (m, 1H), 2.22-2.17 (m, 1H), 1.56 (s, 3H), 1.23 (d, J=6.4 Hz, 3H).
LC-MS (m/z) 292.1 (MH$^+$) $t_R$ (minutes, method 1)=1.90
$[\alpha]_D^{20}$ +41.33° (c=0.10, methanol).

Stereoisomer 1:
600 mg (26%)
$^1$H NMR (CDCl$_3$, 400 MHz): δ 8.60 (s, 1H), 7.44-7.42 (m, 1H), 7.16-7.12 (m, 1H), 5.61 (s, 1H), 4.27 (q, J=6.4 Hz, 1H), 4.00 (s, 3H), 3.99-3.87 (m, 2H), 2.73-2.66 (m, 1H), 2.22-2.18 (m, 1H), 1.57 (s, 3H), 1.23 (d, J=6.0 Hz, 3H).
LC-MS (m/z) 292.1 (MH$^+$) $t_R$ (minutes, method 1)=1.89
$[\alpha]_D^{20}$ −23.67° (c=0.10, methanol).

Example 18

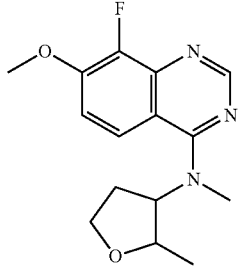

8-Fluoro-7-methoxy-N-methyl-N-(2-methyltetrahydrofuran-3-yl)quinazolin-4-amine

Stereoisomer 1:
To a solution of stereoisomer 2 of example 3 (N-(2,3-dimethyltetrahydrofuran-3-yl)-8-fluoro-7-methoxyquinazolin-4-amine) (150 mg, 0.540 mmol) in dry THF (5 mL) was added a 60% suspension of NaH in mineral oil (32 mg, 0.81 mmol) at 0° C. under N$_2$. The mixture was stirred at 0° C. for 30 min, then CH$_3$I (92 mg, 0.65 mmol) was added. The reaction was stirred for 2 hrs at 0° C. before addition of sat. aq. NH$_4$Cl (5 mL). The crude reaction mixture was extracted with ethyl acetate (3×10 mL). The combined organic phases were washed with brine (5 mL), dried over Na$_2$SO$_4$, and concentrated in vacuo. The residue was purified by flash chromatography using a gradient of petroleum ether and ethyl acetate to give stereoisomer 1 of 8-fluoro-7-methoxy-N-methyl-N-(2-methyltetrahydrofuran-3-yl)quinazolin-4-amine 135 mg (86%).

$^1$H NMR (CDCl$_3$, 400 MHz): δ 8.62 (s, 1H), 7.79 (dd, J=9.6, 2.0 Hz, 1H), 7.17-7.13 (m, 1H), 5.50-5.45 (m, 1H), 4.20-4.16 (m, 1H), 4.07 (s, 3H), 4.04-4.03 (m, 1H), 3.77-3.71 (m, 1H), 3.39 (s, 3H), 2.46-2.42 (m, 1H), 2.33-2.29 (m, 1H), 1.29 (d, J=6.8 Hz, 3H).

LC-MS (m/z) 292.1 (MH$^+$) t$_R$ (minutes, method 2)=1.80

[α]$_D^{20}$ +43.00° (c=0.10, methanol).

Stereoisomer 2:

To a solution of stereoisomer 1 of example 3 (N-(2,3-dimethyltetrahydrofuran-3-yl)-8-fluoro-7-methoxyquinazolin-4-amine) (150 mg, 0.540 mmol) in THF (5 mL) was added a 60% suspension of NaH in mineral oil (32 mg, 0.81 mmol) at 0° C. under N$_2$. The mixture was stirred for 30 min at 0° C., and then methyliodide (92 mg, 0.65 mmol) was added. Stirring was continued for 2 hrs at 0° C. and then sat. aq. NH$_4$Cl (5 mL) was added. The mixture was extracted with ethyl acetate (3×10 mL). The combined organic phases were washed with brine (5 mL), dried over Na$_2$SO$_4$, and concentrated in vacuo. The crude product was purified by flash chromatography using a gradient of petroleum ether and ethyl acetate to give stereoisomer 2 of 8-fluoro-7-methoxy-N-methyl-N-(2-methyltetrahydrofuran-3-yl)quinazolin-4-amine 130 mg (82.5%).

$^1$H NMR (CDCl$_3$, 400 MHz): δ 8.67 (s, 1H), 7.76 (d, J=9.6 Hz, 1H), 7.20-7.16 (m, 1H), 4.83 (brs, 1H), 4.19-4.16 (m, 1H), 4.07-4.02 (m, 5H), 3.31 (s, 3H), 2.50 (brs, 1H), 2.13 (brs, 1H), 1.30 (d, J=6.0 Hz, 3H).

LC-MS (m/z) 292.1 (MH$^+$) t$_R$ (minutes, method 2)=1.82

[α]$_D^{20}$ −30.00° (c=0.10, methanol).

Stereoisomer 3:

To a solution of stereoisomer 3 of example 3 (N-(2,3-dimethyltetrahydrofuran-3-yl)-8-fluoro-7-methoxyquinazolin-4-amine) (150 mg, 0.540 mmol) in THF (5 mL) was added a 60% suspension of NaH in mineral oil (32 mg, 0.81 mmol) at 0° C. under N$_2$ and the mixture was stirred for 30 min. Methyl iodide (77 mg, 0.54 mmol) was added at 0° C. and stirring was continued for 2 hrs at 0° C. The reaction was quenched by sat. aq. NH$_4$Cl (5 mL) and then extracted with ethyl acetate (3×10 mL). The combined organic phases were washed with brine (5 mL), dried over Na$_2$SO$_4$ and concentrated in vacuo. The residue was purified by flash chromatography using a gradient of petroleum ether and ethyl acetate to give stereoisomer 3 of 8-fluoro-7-methoxy-N-methyl-N-(2-methyltetrahydrofuran-3-yl)quinazolin-4-amine (110 mg, 69.8%).

$^1$H NMR (CDCl$_3$, 400 MHz): δ 8.61 (s, 1H), 7.79 (dd, J=9.6, 2.0 Hz, 1H), 7.17-7.13 (m, 1H), 5.49-5.45 (m, 1H), 4.21-4.16 (m, 1H), 4.06 (s, 3H), 4.04-4.02 (m, 1H), 3.77-3.73 (m, 1H), 3.39 (s, 3H), 2.46-2.42 (m, 1H), 2.33-2.29 (m, 1H), 1.29 (d, J=6.4 Hz, 3H).

LC-MS (m/z) 292.1 (MH$^+$) t$_R$ (minutes, method 2)=1.81

[α]$_D^{20}$ −73.00° (c=0.10, methanol).

Stereoisomer 4:

To a solution of stereoisomer 4 of example 3 (N-(2,3-dimethyltetrahydrofuran-3-yl)-8-fluoro-7-methoxyquinazolin-4-amine) (150 mg, 0.541 mmol) in THF (5 mL) was added a 60% suspension of NaH in mineral oil (32 mg, 0.81 mmol) at 0° C. under N2 and the mixture was stirred for 30 min. Then methyliodide (92 mg, 0.65 mmol) stirring was continued for 2 hrs at 0° C. The reaction was quenched by addition of sat. aq. NH$_4$Cl (5 mL). The reaction was extracted with ethyl acetate (3×10 mL). The combined organic phases were washed with brine (5 mL), dried over Na$_2$SO4 and concentrated in vacuo. The crude product was purified by flash chromatography using a gradient of petroleum ether and ethyl acetate to give stereoisomer 4 of 8-fluoro-7-methoxy-N-methyl-N-(2-methyltetrahydrofuran-3-yl)quinazolin-4-amine 120 mg (76.2%).

$^1$H NMR (CDCl$_3$, 400 MHz): δ 8.66 (s, 1H), 7.76 (dd, J=9.6, 2.0 Hz, 1H), 7.20-7.16 (m, 1H), 4.86-4.81 (m, 1H), 4.19-4.14 (m, 1H), 4.07 (s, 3H), 4.06-4.02 (m, 2H), 3.31 (s, 3H), 2.54-2.48 (m, 1H), 2.17-2.10 (m, 1H), 1.30 (d, J=6.4 Hz, 3H). LC-MS (m/z) 292.1 (MH$^+$) t$_R$ (minutes, method 2)=1.82

[α]$_D^{20}$ +90.33° (c=0.10, methanol).

Example 19

N-(2,3-Dimethyltetrahydrofuran-3-yl)-8-fluoro-7-methoxy-N-methylquinazolin-4-amine

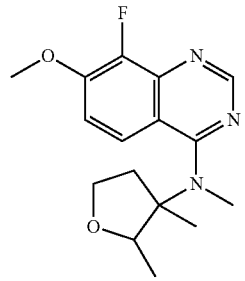

Stereoisomer 1:

To an ice-cold solution of stereoisomer 3 of example 17 of (N-(2,3-dimethyltetrahydrofuran-3-yl)-8-fluoro-7-methoxyquinazolin-4-amine) (200 mg, 0.687 mmol) in THF (10 mL) was added a 60% dispersion of NaH in mineral oil (55 mg, 1.4 mmol). The mixture was stirred at 0° C. for 30 min and then MeI (146 mg, 1.03 mmol) was added. The reaction was warmed to 30° C. and stirred for 2 hrs. H$_2$O (5 mL) was added and the THF was removed in vacuo. The residue was extracted with dichloromethane (2×20 mL). The combined organic phases were washed with H$_2$O (10 mL), dried over Na$_2$SO$_4$ and concentrated in vacuo. The crude product was purified by preparative TLC, using petroleum ether and ethyl acetate 1/1, to give stereoisomer 1 of N-(2,3-dimethyltetrahydrofuran-3-yl)-8-fluoro-7-methoxy-N-methylquinazolin-4-amine
127 mg (60.4%)

$^1$H NMR (CDCl$_3$, 400 MHz): δ 8.66 (s, 1H), 7.71 (dd, J=9.2, 2.0 Hz, 1H), 7.21-7.17 (m, 1H), 4.81 (q, J=6.4 Hz, 1H), 4.06 (s, 3H), 4.04-4.01 (m, 1H), 3.94-3.87 (m, 1H), 3.31 (s, 3H), 2.48-2.40 (m, 1H), 2.17-2.13 (m, 1H), 1.71 (s, 3H), 0.93 (d, J=6.4 Hz, 3H).

LC-MS (m/z) 306.2 (MH$^+$) t$_R$ (minutes, method 1)=1.89

[α]$_D^{20}$ −8.00° (c=0.10, methanol).

Stereoisomer 2:

To an ice-cold solution of stereoisomer 2 of example 17 (N-(2,3-dimethyltetrahydrofuran-3-yl)-8-fluoro-7-methoxy-quinazolin-4-amine) (200 mg, 0.687 mmol) in THF (10 mL) was added a 60% suspension of NaH in mineral oil (55 mg, 1.3 mmol). The reaction was stirred at 0° C. for 30 min and then MeI (146 mg, 1.03 mmol) was added. The reaction was then heated to 30° C. and stirred for 2 hrs. H$_2$O (5 mL) was added to the mixture and THF was removed in vacuo. The residue was extracted with dichloromethane (2×20 mL). The combined organic phases were washed with H$_2$O (10 mL), dried over Na$_2$SO$_4$ and concentrated in vacuo. The crude product was purified by preparative TLC, using petroleum ether and ethyl acetate 1/1 to give stereoisomer 2 of N-(2,3-dimethyltetrahydrofuran-3-yl)-8-fluoro-7-methoxy-N-methylquinazolin-4-amine.

70 mg (33%)

$^1$H NMR (CDCl$_3$, 400 MHz): δ 8.72 (s, 1H), 7.71 (dd, J=9.6, 2.0 Hz, 1H), 7.22-7.18 (m, 1H), 4.38-4.35 (m, 1H), 4.06 (s, 3H), 3.93-3.89 (m, 1H), 3.84-3.80 (m, 1H), 3.22 (s, 3H), 2.54-2.50 (m, 1H), 2.30-2.25 (m, 1H), 1.60 (s, 3H), 1.37 (d, J=6.0 Hz, 3H).

LC-MS (m/z) 306.2 (MH$^+$) t$_R$ (minutes, method 1)=1.93 [α]$_D^{20}$+38.00° (c=0.10, methanol).

Stereoisomer 3:

To an ice-cold solution of stereoisomer 4 of example 17 (N-(2,3-dimethyltetrahydrofuran-3-yl)-8-fluoro-7-methoxy-quinazolin-4-amine) (200 mg, 0.687 mmol) in THF (10 mL) was added a 60% suspension of NaH in mineral oil (55 mg, 1.4 mmol). The mixture was stirred at 0° C. for 30 min and then methyliodide (146 mg, 1.03 mmol) was added. The reaction was then heated to 30° C. and stirred for 2 hrs. H$_2$O (5 mL) was added to the mixture and THF was removed in vacuo. The residue was extracted with dichloromethane (2×20 mL). The combined organic phases were washed with water (10 mL), dried over Na$_2$SO$_4$ and concentrated in vacuo. The crude product was purified by preparative TLC, using petroleum ether and ethyl acetate 1/1, to give stereoisomer 3 of N-(2,3-dimethyltetrahydrofuran-3-yl)-8-fluoro-7-methoxy-N-methylquinazolin-4-amine.

103 mg (49.2%)

$^1$H NMR (CDCl$_3$, 400 MHz): δ 8.66 (s, 1H), 7.72 (dd, J=9.2, 1.6 Hz, 1H), 7.21-7.17 (m, 1H), 4.84-4.80 (m, 1H), 4.06 (s, 3H), 4.04-4.01 (m, 1H), 3.94-3.89 (m, 1H), 3.31 (s, 3H), 2.48-2.40 (m, 1H), 2.17-2.13 (m, 1H), 1.71 (s, 3H), 0.93 (d, J=6.4 Hz, 3H).

LC-MS (m/z) 306.2 (MH$^+$) t$_R$ (minutes, method 1)=1.88 [α]$_D^{20}$+13.00° (c=0.10, methanol).

Stereoisomer 4:

To an ice-cold solution of stereoisomer 1 of example 17 (N-(2,3-dimethyltetrahydrofuran-3-yl)-8-fluoro-7-methoxy-quinazolin-4-amine) (200 mg, 0.687 mmol) in THF (10 mL) was added a 60% suspension of NaH (55 mg, 1.4 mmol). The reaction was stirred at 0° C. for 30 min and then methyliodide (146 mg, 1.03 mmol) was added. The mixture was allowed to warm to 30° C. and stirred for 2 hrs. H$_2$O (5 mL) was added to the mixture and THF was removed in vacuo. The residue was extracted with dichloromethane (2×20 mL). The combined organic phases were washed with H$_2$O (10 mL), dried over Na$_2$SO$_4$ and concentrated in vacuo. The crude product was purified by preparative TLC, using petroleum ether and ethyl acetate=1/1, to give stereoisomer 4 of N-(2,3-dimethyltetrahydrofuran-3-yl)-8-fluoro-7-methoxy-N-methylquinazolin-4-amine.

73 mg (35%)

$^1$H NMR (CDCl$_3$, 400 MHz): δ 8.72 (s, 1H), 7.72 (dd, J=9.2, 2.0 Hz, 1H), 7.22-7.18 (m, 1H), 4.39-4.35 (m, 1H), 4.06 (s, 3H), 3.92-3.89 (m, 1H), 3.84-3.80 (m, 1H), 3.22 (s, 3H), 2.54-2.50 (m, 1H), 2.30-2.25 (m, 1H), 1.60 (s, 3H), 1.37 (d, J=6.4 Hz, 3H).

LC-MS (m/z) 306.2 (MH$^+$) t$_R$ (minutes, method 1)=1.90 [α]$_D^{20}$ −54.33° (c=0.10, methanol).

PDE1 Inhibition Assay

PDE1A, PDE1B and PDE1C assays were performed as follows: the assays was performed in 60 μL samples containing a fixed amount of the PDE1 enzym1 (sufficient to convert 20-25% of the cyclic nucleotide substrate), a buffer (50 mM HEPES pH 7.6; 10 mM MgCl$_2$; 0.02% Tween20), 0.1 mg/ml BSA, 15 nM tritium labelled cAMP and varying amounts of inhibitors. Reactions were initiated by addition of the cyclic nucleotide substrate, and reactions were allowed to proceed for 1 h at room temperature before being terminated through mixing with 20 μL (0.2 mg) yttrium silicate SPA beads (PerkinElmer). The beads were allowed to settle for 1 h in the dark before the plates were counted in a Wallac 1450 Microbeta counter. The measured signals were converted to activity relative to an uninhibited control (100%) and IC$_{50}$ values were calculated using XlFit (model 205, IDBS).

The invention claimed is:

1. A PDE1 enzyme inhibitor having the structure of:
A. a compound of formula (I):

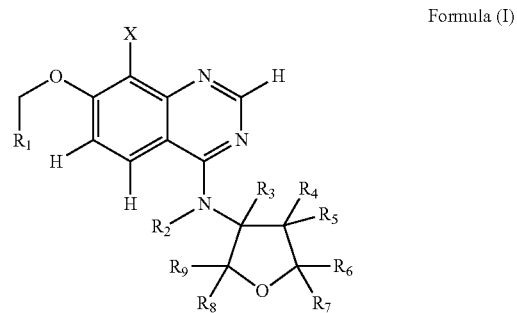

Formula (I)

wherein

X is halogen;

R$_1$ is selected from the group consisting of H and C$_1$-C$_3$ alkyl, wherein the alkyl optionally may be substituted one, two or three times with fluorine;

R$_2$ is selected from the group consisting of H and C$_1$-C$_4$ alkyl, wherein the C$_1$-C$_4$ alkyl optionally is substituted one or more times with one or more substituents independently selected from the group consisting of phenyl, monocyclic 5- or 6-membered heteroaryl, C$_3$-C$_6$ cycloalkyl, fluorine, chlorine, and alkoxy of the form —OR$_{10}$, wherein R$_{10}$ is C$_1$-C$_5$ alkyl; or R$_2$ together with R$_9$ and the atoms connecting them form a saturated five membered ring;

R$_3$ is selected from the group consisting of H and C$_1$-C$_6$ alkyl, wherein the C$_1$-C$_6$ alkyl optionally is substituted one or more times with one or more substituents independently selected from the group consisting of phenyl, monocyclic 5- or 6-membered heteroaryl, C$_3$-C$_6$ cycloalkyl, fluorine, chlorine, and alkoxy of the form —OR$_{10}$, wherein R$_{10}$ is C$_1$-C$_5$ alkyl;

R$_4$ and R$_5$ independently of each other are selected from the group consisting of H, C$_1$-C$_6$ alkyl, C$_3$-C$_6$ cycloalkyl, fluorine, chlorine, hydroxy and alkoxy of the form —OR$_{10}$, wherein the C$_1$-C$_6$ alkyl optionally is substituted one or more times with one or more substituents independently selected from the group consisting of phenyl, monocyclic 5- or 6-membered heteroaryl, C$_3$-C$_6$ cycloalkyl, fluorine, chlorine, and alkoxy of the form —OR$_{10}$, wherein R$_{10}$ is C$_1$-C$_5$ alkyl;

R$_6$ and R$_7$ independently of each other are selected from the group consisting of H and C$_1$-C$_6$ alkyl, wherein the C$_1$-C$_6$ alkyl optionally is substituted one or more times with one or more substituents independently selected from the group consisting of $C_3$-$C_6$ cycloalkyl, fluorine, chlorine, and alkoxy of the form —$OR_{10}$, wherein $R_{10}$ is $C_1$-$C_5$ alkyl;

$R_8$ and $R_9$ independently of each other are selected from the group consisting of H and $C_1$-$C_6$ alkyl, wherein $R_9$, when $R_9$ is a $C_1$-$C_6$ alkyl, may form a saturated aliphatic five membered ring with $R_2$, wherein the $C_1$-$C_6$ alkyl optionally is substituted one or more times with one or more substituents independently selected from the group consisting of $C_3$-$C_6$ cycloalkyl, fluorine, chlorine, and alkoxy of the form —$OR_{10}$, wherein $R_{10}$ is $C_1$-$C_5$ alkyl;

or

B. a pharmaceutically acceptable acid addition salt of said compound of formula (I), a racemic mixture of said compound of formula (I), a corresponding enantiomer and/or optical isomer of said compound of formula (I), a polymorphic form of said compound of formula (I) or a tautomeric form of said compound of formula (I).

2. The PDE1 enzyme inhibitor according to claim 1, wherein $R_2$ of said compound of formula (I) is H or —$CH_3$.

3. The PDE1 enzyme inhibitor according to claim 1, wherein at least one of $R_6$ and $R_7$ of said compound of formula (I) is H.

4. The PDE1 enzyme inhibitor according to claim 3, wherein both $R_6$ and $R_7$ of said compound of formula (I) are H.

5. The PDE1 enzyme inhibitor according to claim 1, wherein at least four of $R_3$ to $R_9$ of said compound of formula (I) are H.

6. The PDE1 enzyme inhibitor according to claim 1, wherein $R_2$ and $R_9$ of said compound of formula (I) form a five-membered saturated aliphatic ring.

7. The PDE1 enzyme inhibitor according to claim 1, wherein when any of $R_3$, $R_4$ or $R_5$ of said compound of formula (I) are alkyl, then at most one of them is substituted at most once with phenyl or monocyclic 5- or 6-membered heteroaryl.

8. The PDE1 enzyme inhibitor of claim 1, wherein X of said compound of formula (I) is fluorine.

9. The PDE1 enzyme inhibitor of claim 1, wherein X of said compound of formula (I) is chlorine.

10. The PDE1 enzyme inhibitor according to claim 1, wherein said compound of formula I is selected from the group consisting of:
  (1) 8-fluoro-7-methoxy-N-(3-methyltetrahydrofuran-3-yl)quinazolin-4-amine;
  (2) 8-fluoro-7-methoxy-N-methyl-N-(tetrahydrofuran-3-yl)quinazolin-4-amine;
  (3) 8-chloro-7-methoxy-N-(tetrahydrofuran-3-yl)quinazolin-4-amine;
  (4) 8-fluoro-7-methoxy-N-(2-methyltetrahydrofuran-3-yl)quinazolin-4-amine;
  (5) 8-chloro-7-methoxy-N-(2-methyltetrahydrofuran-3-yl)quinazolin-4-amine;
  (6) 8-chloro-7-methoxy-N-methyl-N-(tetrahydrofuran-3-yl)quinazolin-4-amine;
  (7) 8-chloro-7-methoxy-N-(3-methyltetrahydrofuran-3-yl)quinazolin-4-amine;
  (8) cis-4-(8-fluoro-7-methoxyquinazolin-4-yl)hexahydro-2H-furo[3,2-b]pyrrole;
  (9) cis-4-(8-chloro-7-methoxyquinazolin-4-yl)hexahydro-2H-furo[3,2-b]pyrrole;
  (10) cis-4-(8-bromo-7-methoxyquinazolin-4-yl)hexahydro-2H-furo[3,2-b]pyrrole;
  (11) 8-chloro-7-methoxy-N-methyl-N-(3-methyltetrahydrofuran-3-yl)quinazolin-4-amine;
  (12) 8-chloro-N-(2,3-dimethyltetrahydrofuran-3-yl)-7-methoxyquinazolin-4-amine;
  (13) 8-chloro-N-(2,3-dimethyltetrahydrofuran-3-yl)-7-methoxy-N-methylquinazolin-4-amine;
  (14) 8-chloro-7-methoxy-N-methyl-N-(2-methyltetrahydrofuran-3-yl)quinazolin-4-amine;
  (15) 8-fluoro-7-methoxy-N-methyl-N-(3-methyltetrahydrofuran-3-yl)quinazolin-4-amine;
  (16) 8-fluoro-7-methoxy-N-(tetrahydrofuran-3-yl)quinazolin-4-amine;
  (17) N-(2,3-dimethyltetrahydrofuran-3-yl)-8-fluoro-7-methoxyquinazolin-4-amine;
  (18) 8-fluoro-7-methoxy-N-methyl-N-(2-methyltetrahydrofuran-3-yl)quinazolin-4-amine;
  and
  (19) N-(2,3-dimethyltetrahydrofuran-3-yl)-8-fluoro-7-methoxy-N-methylquinazolin-4-amine.

11. The PDE1 enzyme inhibitor according to claim 2, wherein at least one of $R_6$ and $R_7$ of said compound of formula (I) is H.

12. The PDE1 enzyme inhibitor according to claim 11, wherein both $R_6$ and $R_7$ of said compound of formula (I) are H.

13. A pharmaceutical composition comprising the PDE1 enzyme inhibitor of claim 1 and one or more pharmaceutically acceptable carriers or diluents.

14. The pharmaceutical composition of claim 13, wherein:
  (A) $R_2$ of said compound of formula I is H or —$CH_3$;
  (B) at least one of $R_6$ and $R_7$ of said compound of formula I is H;
  (C) at least four of $R_3$ to $R_9$ of said compound of formula I are H;
  (D) $R_2$ and $R_9$ of said compound of formula I form a five-membered saturated aliphatic ring;
  (E) when any of $R_3$, $R_4$ or $R_5$ of said compound of formula I are alkyl, then at most one of them is substituted at most once with phenyl or monocyclic 5- or 6-membered heteroaryl;
  or
  (F) X of said compound of formula I is fluorine or chlorine.

15. The pharmaceutical composition of claim 13, wherein said compound of formula I is selected from the group consisting of:
  (1) 8-fluoro-7-methoxy-N-(3-methyltetrahydrofuran-3-yl)quinazolin-4-amine;
  (2) 8-fluoro-7-methoxy-N-methyl-N-(tetrahydrofuran-3-yl)quinazolin-4-amine;
  (3) 8-chloro-7-methoxy-N-(tetrahydrofuran-3-yl)quinazolin-4-amine;
  (4) 8-fluoro-7-methoxy-N-(2-methyltetrahydrofuran-3-yl)quinazolin-4-amine;
  (5) 8-chloro-7-methoxy-N-(2-methyltetrahydrofuran-3-yl)quinazolin-4-amine;
  (6) 8-chloro-7-methoxy-N-methyl-N-(tetrahydrofuran-3-yl)quinazolin-4-amine;
  (7) 8-chloro-7-methoxy-N-(3-methyltetrahydrofuran-3-yl)quinazolin-4-amine;
  (8) cis-4-(8-fluoro-7-methoxyquinazolin-4-yl)hexahydro-2H-furo[3,2-b]pyrrole;
  (9) cis-4-(8-chloro-7-methoxyquinazolin-4-yl)hexahydro-2H-furo[3,2-b]pyrrole;
  (10) cis-4-(8-bromo-7-methoxyquinazolin-4-yl)hexahydro-2H-furo[3,2-b]pyrrole;

(11) 8-chloro-7-methoxy-N-methyl-N-(3-methyltetrahydrofuran-3-yl)quinazolin-4-amine;
(12) 8-chloro-N-(2,3-dimethyltetrahydrofuran-3-yl)-7-methoxyquinazolin-4-amine;
(13) 8-chloro-N-(2,3-dimethyltetrahydrofuran-3-yl)-7-methoxy-N-methylquinazolin-4-amine;
(14) 8-chloro-7-methoxy-N-methyl-N-(2-methyltetrahydrofuran-3-yl)quinazolin-4-amine;
(15) 8-fluoro-7-methoxy-N-methyl-N-(3-methyltetrahydrofuran-3-yl)quinazolin-4-amine;
(16) 8-fluoro-7-methoxy-N-(tetrahydrofuran-3-yl)quinazolin-4-amine;
(17) N-(2,3-dimethyltetrahydrofuran-3-yl)-8-fluoro-7-methoxyquinazolin-4-amine;
(18) 8-fluoro-7-methoxy-N-methyl-N-(2-methyltetrahydrofuran-3-yl)quinazolin-4-amine;
and
(19) N-(2,3-dimethyltetrahydrofuran-3-yl)-8-fluoro-7-methoxy-N-methylquinazolin-4-amine.

* * * * *